United States Patent
Mauldin, Jr. et al.

(10) Patent No.: US 9,949,722 B2
(45) Date of Patent: Apr. 24, 2018

(54) SYSTEM AND METHOD FOR BINDING DYNAMICS OF TARGETED MICROBUBBLES

(71) Applicant: University of Virginia Patent Foundation, Charlottesville, VA (US)

(72) Inventors: F. William Mauldin, Jr., Charlottesville, VA (US); Shiying Wang, Charlottesville, VA (US); John A. Hossack, Charlottesville, VA (US); Alexander L. Klibanov, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 509 days.

(21) Appl. No.: 14/559,422

(22) Filed: Dec. 3, 2014

(65) Prior Publication Data

US 2015/0150534 A1    Jun. 4, 2015

Related U.S. Application Data

(60) Provisional application No. 61/911,068, filed on Dec. 3, 2013.

(51) Int. Cl.
*A61B 8/08* (2006.01)
*G06T 7/00* (2017.01)
*A61B 8/00* (2006.01)

(52) U.S. Cl.
CPC ............ *A61B 8/481* (2013.01); *G06T 7/0016* (2013.01); *A61B 8/0891* (2013.01); *A61B 8/587* (2013.01);

(Continued)

(58) Field of Classification Search
CPC ....... A61B 8/481; A61B 8/587; A61B 8/0891; G06T 7/0016; G06T 2207/30104; G06T 2207/10132
See application file for complete search history.

(56) References Cited

U.S. PATENT DOCUMENTS

| 7,402,136 | B2 | 7/2008 | Hossack et al. |
| 7,699,776 | B2 | 4/2010 | Walker et al. |

(Continued)

FOREIGN PATENT DOCUMENTS

| WO | WO-03/075769 A1 | 9/2003 |
| WO | WO-2004/064619 A2 | 8/2004 |

(Continued)

OTHER PUBLICATIONS

Mauldin, Jr. et al. "Isolation of Signal From Stationary Microbubbles Adhered to Vessel Walls Using an Adaptive Regression Filtering Technique." IEEE Intl Ultrasonics Symp Proc (2010), pp. 1121-1124.*

(Continued)

*Primary Examiner* — Long V Le
*Assistant Examiner* — Angela M Hoffa
(74) *Attorney, Agent, or Firm* — Schwegman Lundberg & Woessner, P.A.

(57) ABSTRACT

An ultrasound system and method that can include: a receive beamformer configured to receive signals from a transducer; a processor coupled to the receive beamformer, the processor configured to: analyze echo data reflected from a region of interest, the echo data elicited by a transmitted pulse sequence; using the echo data, determine a central tendency of a signal magnitude from regions of adherent microbubbles over time within the region of interest; determine a time series of the signal magnitude; using the time series, determine an initial signal magnitude parameter;

(Continued)

obtain a saturated signal parameter and a residual signal parameter using the time series; and determine a relative indication of information indicative of the residual signal magnitude versus the saturated signal magnitude.

19 Claims, 18 Drawing Sheets
(3 of 18 Drawing Sheet(s) Filed in Color)

(52) U.S. Cl.
CPC .............. *G06T 2207/10132* (2013.01); *G06T 2207/30104* (2013.01)

(56) References Cited

U.S. PATENT DOCUMENTS

| | | |
|---|---|---|
| 7,750,537 B2 | 7/2010 | Hossack et al. |
| 8,057,392 B2 | 11/2011 | Hossack et al. |
| 8,093,782 B1 | 1/2012 | Hossack |
| 8,306,293 B2 | 11/2012 | Walker et al. |
| 8,440,167 B2 | 5/2013 | Beller et al. |
| 8,548,759 B2 | 10/2013 | Walker et al. |
| 8,622,911 B2 | 1/2014 | Hossack et al. |
| 9,002,080 B2 * | 4/2015 | Mauldin, Jr. ........ G06K 9/6247 382/100 |
| 9,603,582 B2 * | 3/2017 | Chen ........................ A61B 8/12 |
| 9,629,935 B2 * | 4/2017 | Yeh ........................ A61B 6/481 |
| 2007/0016022 A1 | 1/2007 | Blalock et al. |
| 2007/0016044 A1 | 1/2007 | Blalock et al. |
| 2007/0059247 A1 | 3/2007 | Lindner et al. |
| 2010/0063399 A1 | 3/2010 | Walker et al. |
| 2010/0168578 A1 | 7/2010 | Garson, Jr. et al. |
| 2010/0268086 A1 | 10/2010 | Walker et al. |
| 2010/0298709 A1 * | 11/2010 | Needles .................. A61B 8/06 600/458 |
| 2010/0331686 A1 | 12/2010 | Hossack et al. |
| 2011/0137175 A1 | 6/2011 | Hossack et al. |
| 2012/0029356 A1 | 2/2012 | Hossack et al. |
| 2012/0053460 A1 | 3/2012 | Blalock et al. |
| 2012/0209116 A1 | 8/2012 | Hossack et al. |
| 2012/0244564 A1 | 9/2012 | Walker et al. |
| 2012/0296213 A1 | 11/2012 | Mauldin, Jr. et al. |
| 2013/0094729 A1 * | 4/2013 | Mauldin, Jr. ........ G06K 9/6247 382/128 |
| 2013/0251633 A1 * | 9/2013 | Borden .................. A61B 8/085 424/9.2 |
| 2014/0046186 A1 | 2/2014 | Mauldin, Jr. et al. |
| 2014/0142468 A1 | 5/2014 | Hossack et al. |
| 2014/0236005 A1 * | 8/2014 | Chen ........................ A61B 8/12 600/433 |
| 2016/0199033 A1 * | 7/2016 | Yeh ........................ A61B 6/481 382/131 |

FOREIGN PATENT DOCUMENTS

| | | |
|---|---|---|
| WO | WO-2004/064620 A2 | 8/2004 |
| WO | WO-2004/065978 A2 | 8/2004 |
| WO | WO-2006/042067 A2 | 4/2006 |
| WO | WO-2007/027584 A2 | 3/2007 |
| WO | WO-2008/154632 A2 | 12/2008 |
| WO | WO-2009/055720 A1 | 4/2009 |
| WO | WO-2010/021709 A1 | 2/2010 |
| WO | WO-2010/062557 A2 | 6/2010 |
| WO | WO-2010/119363 A1 | 10/2010 |
| WO | WO-2011/011539 A1 | 1/2011 |
| WO | WO-2011/035162 A1 | 3/2011 |
| WO | WO-2011/094585 A1 | 8/2011 |
| WO | WO-2012/148985 A1 | 11/2012 |
| WO | WO-2013/188625 A1 | 12/2013 |

OTHER PUBLICATIONS

Gessner et al. "Radiation force-enhanced targeted imaging and near real-time molecular imaging using a dial-frequency high-resolution transducer." IEEE Intl Ultrasonic Symp Proc (2009), pp. 9-12.*
Wang et al. "Ultrasound Molecular Imaging with Modulated Acoustic Radiation Force-based Beam Sequence in Mouse Abdominal Aorta: A Feasibility Study." IEEE Intl Ultrasonic Symp Proc (2015), 4 pages.*
Wang et al. "Binding dynamics of targeted microbubbles in response to modulated acoustic radiation force." Phys Med Biol, vol. 59 (Dec. 30, 2013) pp. 465-484.*
Dayton, P., et al., "Acoustic radiation force in vivo: a mechanism to assist targeting of microbubbles", Ultrasound Med Biol. 25, (1999), 1195-1201.
Dayton, P. A., et al., "The magnitude of radiation force on ultrasound contrast agents", *J Acoustic Soc Am. 112*, (2002), 2183-2192.
Gessner, R. C., et al., "An in vivo validation of the application of acoustic radiation force to enhance the diagnostic utility of molecular imaging using 3-d ultrasound", *Ultrasound Med Biol. 38*, (2012), 651-660.
Hammer, D. A., et al., "A dynamical model for receptor-mediated cell adhesion to surfaces in viscous shear flow", *Cell Biophys.* (1989), 139-173.
Hossack, John A., "Specialized, High Performance, Ultrasound Transducer Substrates and Related Method Thereof", U.S. Appl. No. 13/329,965, filed Dec. 19, 2011, 18 pgs.
Hu, X., et al., "A sensitive TLRH targeted imaging technique for ultrasonic molecular imaging", *IEEE Trans. Ultrason. Ferroelectr. Freq. Control 57*, (2010), 305-316.
Klibanov, A. L., et al., "Evaluation of quantitative parameters of the interaction of antibody-bearing liposomes with target antigens", *Anal Biochem. 150*, (1985), 251-257.
Mauldin, F. W., et al., "Real-time targeted molecular imaging using singular value spectra properties to isolate the adherent microbubble signal", *Phys Med Biol. 57*, (2012), 5275-5293.
Needles, A., et al., "A method for differentiating targeted microbubbles in real time using subharmonic micro-ultrasound and interframe filtering", *Ultrasound Med Biol. 35*, (2009), 1564-1573.
Patil, A. V., et al., "Dual frequency method for simultaneous translation and real-time imaging of ultrasound contrast agents within large blood vessels", *Ultrasound Med Biol. 35*, (2009), 2021-2030.
Patil, A. V., et al., "Real-time technique for improving molecular imaging and guiding drug delivery in large blood vessels: in vitro and ex vivo results", *Mol Imaging. 10*, (2011), 238-247.
Phillips, P., "Contrast pulse sequences (CPS): imaging nonlinear microbubbles", *IEEE Ultrason. Symp.*, (2001), 1739-1745.
Phillips, P., et al., "Contrast-agent detection and quantification", *Eur Radiol. 14 Suppl 8*, (2004), p. 4-p. 10.
Pysz, M A., et al., "Fast microbubble dwell-time based ultrasonic molecular imaging approach for quantification and monitoring of angiogenesis in cancer", *Quant Imaging Med.Surg. 2*, (2012), 68-80.
Pysz, M. A., et al., "Quantitative assessment of tumor angiogenesis using real-time motion-compensated contrast-enhanced ultrasound imaging", *Angiogenesis 15*, (2012), 433-442.

* cited by examiner

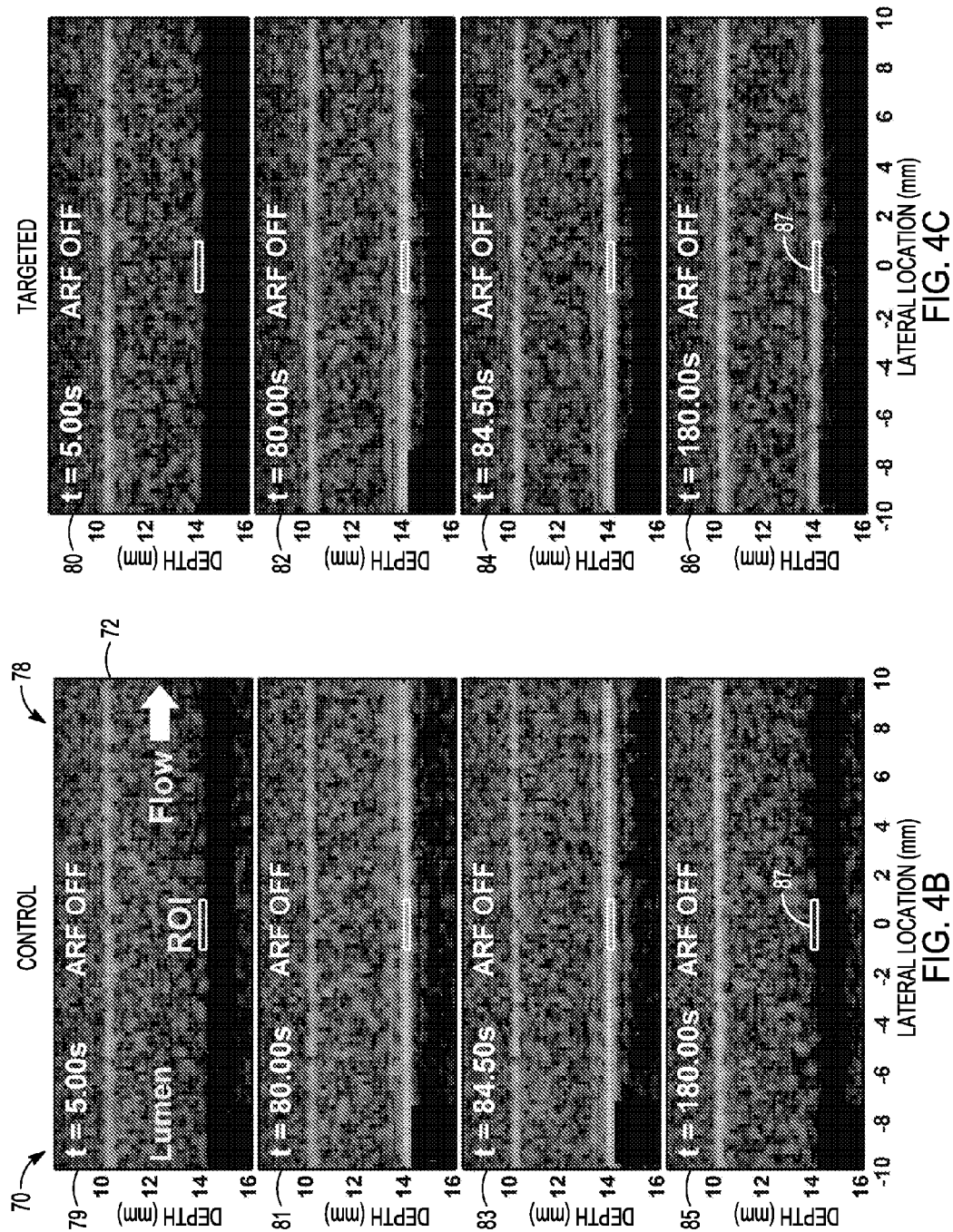

SYSTEM AND METHOD FOR BINDING DYNAMICS OF TARGETED MICROBUBBLES

CLAIM OF PRIORITY

This patent application claims the benefit of priority of Wang et. al. U.S. Provisional Patent Application Ser. No. 61/911,068, entitled "System and Method for Binding Dynamics of Targeted Microbubbles in Response to Modulated Acoustic Radiation Force," filed on Dec. 3, 2013, which is hereby incorporated by reference herein in its entirety.

STATEMENT REGARDING FEDERALLY SPONSORED RESEARCH OR DEVELOPMENT

This invention was made with government support under R01EB001826 and R01HL111077 awarded by the National Institutes of Health (NIH). The government has certain rights in the invention.

BACKGROUND

Microbubbles—comprising low solubility gas bubbles (less than 10 µm in diameter) stabilized with a shell (lipid, protein, or polymer) can be used as an ultrasound contrast agent. Targeted microbubbles have been fabricated by incorporating a microbubble shell with ligands specific to molecular markers (e.g. ICAM-1 and P-selectin for cardiovascular-related diseases). These ligands have been shown to allow microbubbles to attach to specific regions of a vascular endothelium through the specific ligand-receptor bond, thereby enabling applications for both targeted molecular imaging and targeted gene/drug delivery. In order to increase the binding efficacy of targeted microbubbles to potential binding sites, especially in large blood vessel environments, acoustic radiation force (ARF) can be applied. In addition, targeted microbubbles incorporated with multiple ligands can be used to further increase adhesion to the vessel wall.

The detection and enhancement of signals derived from ligand-receptor bound microbubbles ("specifically bound adherent microbubbles") and suppression of surrounding tissue and freely circulating microbubbles can be a central technical challenge in ultrasound-based targeted molecular imaging. Nonlinear signal detection methods (e.g. pulse inversion or harmonic imaging) have been used to eliminate signals from surrounding tissue. Thereafter, signals from "free" microbubbles have been suppressed by lengthy waiting periods (e.g. 15-30 min) to clear the vessel lumen, or by low-pass interframe filtering from recently developed real-time targeted molecular imaging techniques. Previous approaches are only capable of detecting adherent microbubbles and cannot distinguish between non-specific molecular binding (undesirable "signal"), which increases with applied ARF, and specific binding (desirable "signal"). Therefore, all of the previously described techniques require control groups using deactivated microbubbles (or a non-activated flow phantom in an in vitro test) to estimate the non-specific adhesion "background" signal so that a true picture of specifically bound microbubbles can be found.

The presence of the targeted molecular entity along a vascular wall can be assumed if there is a significant increase in adherent microbubbles between control and targeted groups. A consequence of having to use a control group in addition to a test group is that multiple microbubble populations may need to be used resulting in very long procedure times, up to 30-40 minutes, as it often requires at least 20 minutes for microbubbles to clear the vasculature after a single injection. In addition, the specificity of the detection of molecular targets can be limited due to detection of an undesired positive signal from control groups (the control group microbubble signal is often 20% or more of targeted group signal).

Overview

The present inventors have recognized the need for a system and method that can analyze a targeted microbubble procedure in real-time, without the need for a control group test. In this disclosure, the present inventors show that measurements of microbubble binding dynamics under modulated ARF can provide enhanced detection of targeted microbubble adhesion that can differentiate from non-specific binding in blood vessel environments. A model for microbubble dynamics in response to a modulated ARF transmitted pulse sequence is disclosed and the model is compared to experimental observation in control and targeted flow phantom experiments. The relationship between experimental conditions and model parameters are determined for varied flow velocities, microbubble concentrations, and time averaged ARF intensity. Parameters uniquely obtainable from microbubble response to modulated radiation force can be utilized for detection of targeted adhesion independent of control populations.

This overview is intended to provide an overview of subject matter of the present patent application. It is not intended to provide an exclusive or exhaustive explanation of the invention. The detailed description is included to provide further information about the present patent application.

To further illustrate the injection instrument and method disclosed herein, a non-limiting list of examples is provided here:

In Example 1, an ultrasound system can comprise: a receive beamformer configured to receive signals from a transducer; a processor coupled to the receive beamformer, the processor configured to: analyze echo data reflected from a region of interest, the echo data elicited by a transmitted pulse sequence; using the echo data, determine a central tendency of a signal magnitude from regions of adherent microbubbles over time within the region of interest; determine a time series of the signal magnitude; using the time series, determine an initial signal magnitude parameter; obtain a saturated signal parameter and a residual signal parameter using the time series; and determine a relative indication of information indicative of the residual signal magnitude versus the saturated signal magnitude.

In Example 2, the ultrasound system of Example 1 can optionally be configured such that the processor is configured to obtain a ratio, the ratio comparing: i) a concentration of microbubbles that have specifically adhered to a channel wall in the region of interest to ii) a full saturation of adherent microbubbles in the region of interest.

In Example 3, the ultrasound system of Example 2 can optionally be configured such that the ratio is proportional to a ratio of the residual signal magnitude parameter to the saturated signal magnitude parameter.

In Example 4, the ultrasound system of Example 3 can optionally be configured such that the ratio expressed as a percentage is:

$$R_{resid} = \left(\frac{M_{resid} - M_{init}}{M_{satu} - M_{init}}\right) \times 100\%$$

In Example 5, the ultrasound system of any one or any combination of Examples 1-4 can optionally be configured such that the transmitted pulse sequence includes a series of frames, each frame including an imaging pulse and a portion of the frames including an acoustic radiation force pulse.

In Example 6, the ultrasound system of any one or any combination of Examples 1-5 can optionally be configured such that the transmitted pulse sequence includes imaging pulses and acoustic radiation force pulses.

In Example 7, the ultrasound system of Example 6 can optionally be configured such that the transmitted pulse sequence includes a first temporal period including acoustic radiation force pulses and a second temporal period not including acoustic radiation force pulses.

In Example 8, the ultrasound system of any one or any combination of Examples 6-7 can optionally be configured such that the transmitted pulse sequence is at least 100 seconds in duration, the transmitted pulse sequence having an initial temporal period not including acoustic radiation force pulses, an intermediate temporal period including acoustic radiation force pulses, and a final temporal period not including acoustic radiation force pulses.

In Example 9, the ultrasound system of any one or any combination of Examples 6-8 can optionally be configured such that the transmitted pulse sequence is at least 180 seconds in duration, the transmitted pulse sequence having an initial temporal period of 10 seconds duration not including acoustic radiation force pulses, an intermediate temporal period of 70 seconds duration including acoustic radiation force pulses, and a final temporal period of 100 seconds duration not including acoustic radiation force pulses.

In Example 10, the ultrasound system of any one or any combination of Examples 7-9 can optionally be configured such that the first temporal period includes a signal magnitude dynamic response that can be described as:

$$M_{rise}(t) = M_{satu} - (M_{satu} - M_{init}) \times e^{-\frac{t}{\tau_{rise}}},$$

and the second temporal period includes a signal magnitude decay response that can be described as:

$$M_{decay}(t) = M_{resid} - (M_{resid} - M_{max}) \times e^{-\frac{t}{\tau_{decay}}},$$

wherein $M_{max}$ is a maximum signal magnitude measured immediately after a cessation of the acoustic radiation force.

In Example 11 a method of measuring microbubble dynamics can comprise: injecting targeting microbubbles into a flowing fluid system; analyzing echo data reflected from a region of interest, the echo data elicited by a transmitted pulse sequence; using the echo data, determining a central tendency of a signal magnitude from regions of adherent microbubbles over time within the region of interest; determining a time series of the signal magnitude; using the time series, determining an initial signal magnitude parameter; obtaining a saturated signal parameter and a residual signal parameter using the time series; and determining a relative indication of information indicative of the residual signal magnitude versus the saturated signal magnitude.

In Example 12, the method of Example 11 can optionally be configured to comprise: obtaining a ratio, the ratio comparing: i) a concentration of microbubbles that have specifically adhered to a channel wall in the region of interest to ii) a full saturation of adherent microbubbles in the region of interest.

In Example 13 the method of Example 12 can optionally be configured such that the ratio is proportional to a ratio of the residual signal magnitude parameter to the saturated signal magnitude parameter.

In Example 14 the method of any one or any combination of Examples 11-13 can optionally be configured such that the transmitted pulse sequence includes a series of frames, each frame having imaging pulses and a portion of the series of frames including acoustic radiation force pulses.

In Example 15, the method of any one or any combination of Examples 11-14 can optionally be configured such that the transmitted pulse sequence includes imaging pulses and acoustic radiation force pulses.

In Example 16 the method of Example 15 can optionally be configured such that the transmitted pulse sequence includes a first temporal period including acoustic radiation force pulses and a second temporal period not including acoustic radiation force pulses.

In Example 17, a non-transitory machine readable medium embodying a set of instructions that, when executed by a processor, cause the processor to perform operations that can comprise: analyzing echo data reflected from a region of interest, the echo data elicited by a transmitted pulse sequence; using the echo data, determining a central tendency of a signal magnitude from regions of adherent microbubbles over time within the region of interest; determining a time series of the signal magnitude; using the time series, determining an initial signal magnitude parameter; obtaining a saturated signal parameter and a residual signal parameter using the time series; and determining a relative indication of information indicative of the residual signal magnitude versus the saturated signal magnitude.

In Example 18 the non-transitory machine readable medium of Example 17 embodying a set of instructions that, when executed by a processor, cause the processor to perform operations that can comprise obtaining a ratio, the ratio comparing: i) a concentration of microbubbles that have specifically adhered to a channel wall in the region of interest to ii) a full saturation of adherent microbubbles in the region of interest.

In Example 19 the non-transitory machine readable medium of Example 18 can optionally be configured such that the ratio is proportional to a ratio of the residual signal magnitude parameter to the saturated signal magnitude parameter.

In Example 20 the non-transitory machine readable medium of any one or any combination of Examples 17-19 can optionally be configured such that the transmitted pulse sequence includes imaging pulses and acoustic radiation force pulses and the transmitted pulse sequence includes a first temporal period including acoustic radiation force pulses and a second temporal period not including acoustic radiation force pulses.

In Example 21, the ultrasound system, method, or non-transitory machine readable medium of any one or any combination of Examples 1-20 can optionally be configured such that all elements, operations, or other options recited are available to use or select from.

Example 22 can include, or can optionally be combined with any portion or combination of any portions of any one or more of Examples 1 through 20 to include, subject matter that can include means for performing any one or more of the functions of Examples 1 through 20, or a machine-readable medium including instructions that, when performed by a machine, cause the machine to perform any one or more of the functions of Examples 1 through 20.

These and other examples and features of the present injection instrument and method will be set forth in part in the following Detailed Description. This Overview is intended to provide non-limiting examples of the present subject matter—it is not intended to provide an exclusive or exhaustive explanation. The Detailed Description below is included to provide further information about the present injection instrument and method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4B illustrates B-mode images of control channel groups that were displayed at 50 dB dynamic range showing the channel lumen of control channels at different times, accordance with at least one example of the present subject matter.

FIG. 4C illustrates B-mode images of targeted channel groups that were displayed at 50 dB dynamic range showing the channel lumen of targeted channels at different times, accordance with at least one example of the present subject matter.

DETAILED DESCRIPTION

Figure 1:
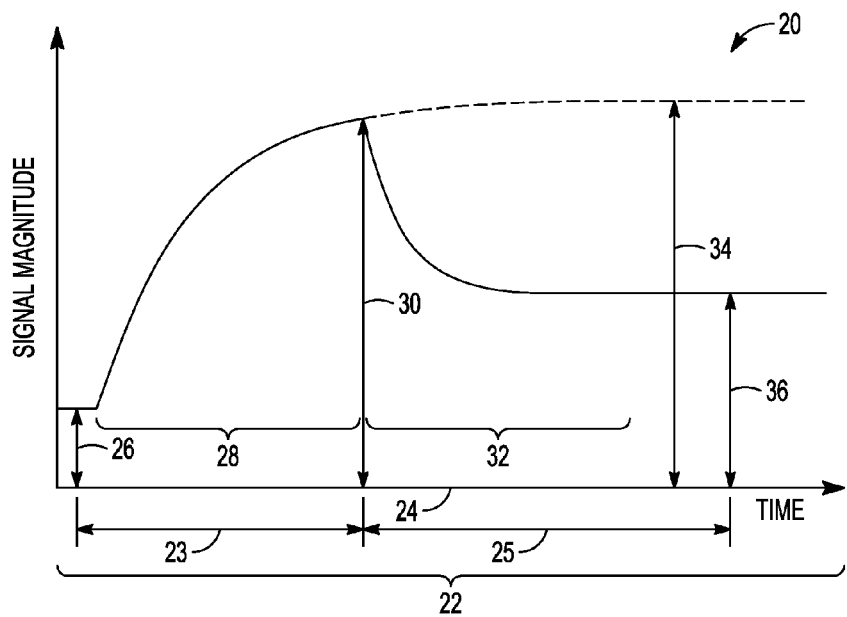
FIG. 1 illustrates a representative example of an ultrasound signal magnitude curve determined by Equations (5) and (6) (hereinafter EQN.) in response to a modulated ARF input, in accordance with at least one example of the present subject matter.

Suitable models that can predict microbubble binding dynamics in response to modulated, acoustic radiation force (ARF) can be important for enhanced detection of specifically, versus non-specifically, bound adherent microbubbles as they can guide selection of parameter extraction for optimal detection sensitivity and specificity. A previous study has provided a theoretical model for cell-to-cell adhesion when the adhesion is mediated by reversible specific bonds attached on a cell membrane. The kinetic equation can be written as:

$$\frac{dN_b}{dt} = k_+ N_{1f} N_{2f} - k_- N_b \quad \text{(EQN. 1)}$$

where $N_b$ is the number of bound receptors per unit area which serve to bridge the cells; $N_{1f}$ and $N_{2f}$ are corresponding numbers of unbound receptors from two cells; $k_+$ and $k_-$ are reaction rate constants for association and disassociation processes, respectively. Based on this model, a previous study developed dynamic models for receptor-mediated adhesion of cells under a shear field of fluid within a surface coated fluid channel by analyzing the force balance of an individual cell attached to a channel wall. Thereafter, another previous study implemented the computational model on both single- and dual-targeted microbubbles to improve selection of ligands and binding strength. However, the computational models for adhesive dynamics of targeted microbubbles were based on single microbubble analysis. In addition, the effects of ARF were not considered.

Unlike micro analysis of single microbubbles, another previous study developed a model for the macro analysis of targeted liposomes through experiments in multiwall plates. Time courses of bound liposome concentration and dissociation constants were obtained. The binding and detachment dynamics of microbubbles targeted to P-selectin in a parallel-plate flow chamber were also previously studied. Influence of flow shear stress and surface density of targeted receptor on binding and detachment dynamics were investigated. However, the effects of ARF on microbubble binding dynamics were not included.

In order to model the binding dynamics of targeted microbubbles in response to modulated ARF, the present inventors have developed a kinetic equation of adherent microbubbles on the bottom surface of a vessel that can be described in an analogous manner to (EQN. 1):

$$\frac{dN_{AMB}}{dt} = k_+(N_{FMB}^d)N_B - k_- N_{AMB} \quad \text{(EQN. 2)}$$

where $N_{AMB}$ is the number of adherent microbubbles per unit area on the surface of a bottom wall; $N_{FMB}$ is the number of freely circulating microbubbles per unit volume within an effective boundary layer near the bottom surface; d is the effective boundary layer thickness; $N_B$ is the number of receptors (complementary to the ligands attached to a microbubble shell) per unit area on the bottom surface of the vessel; $k_+$ and $k_-$ are reaction rate constants for association and disassociation process, respectively. Both reaction rate constants were expected to be functions of both ARF and flow shear force.

With application of constant ARF, freely circulating microbubble concentration within the effective boundary layer near the bottom surface increases. As a result, the concentration of adherent microbubbles increases. If surface concentration of receptors and flow velocity are constant, according to (EQN. 2), $N_{AMB}$ during application of ARF should be:

$$N_{AMB} = \frac{k_+^{ON}}{k_-^{ON}}(N_{FMB}^{ON}d)N_B - \left(\frac{k_+^{ON}}{k_-^{ON}}(N_{FMB}^{ON}d)N_B - N_{AMB}^{ON}\right) \times e^{-\frac{t}{\frac{1}{k_-^{ON}}}} \quad \text{(EQN. 3)}$$

where $N_{FMB}^{ON}$ is the freely circulating microbubble concentration within the effective boundary layer near the bottom surface with application of ARF; $N_{AMB}^{ON}$ is the initial number of adherent microbubbles per unit area when ARF starts; $k_+^{ON}$ and $k_-^{ON}$ are reaction rate constants for association and disassociation process, respectively, with application of ARF. After cessation of ARF, concentration of freely circulating microbubbles within the effective boundary layer near the bottom surface decreases, resulting in a decaying signal magnitude. Assuming the acoustic pressure of imaging pulses is negligible, according to (EQN. 2), $N_{AMB}$ after cessation of ARF should be:

$$N_{AMB} = \frac{k_+^{OFF}}{k_-^{OFF}}(N_{FMB}^{OFF}d)N_B - \left(\frac{k_+^{OFF}}{k_-^{OFF}}(N_{FMB}^{OFF}d)N_B - N_{AMB}^{OFF}\right) \times e^{-\frac{t}{1/k_-^{OFF}}} \quad \text{(EQN. 4)}$$

where $N_{FMB}^{OFF}$ is the freely circulating microbubble concentration within the effective boundary layer near the bottom surface after cessation of ARF; $N_{AMB}^{OFF}$ is the initial number of adherent microbubbles per unit area when ARF stops. $k_+^{OFF}$ and $k_-^{OFF}$ are reaction rate constants for association and disassociation process, respectively, after cessation of ARF.

In the present disclosure, an ultrasound signal magnitude, M(t), is used as a quantity that is assumed to be directly proportional to adherent microbubble concentration. This assumption has been shown to be valid at low microbubble concentration and mechanical index, by a previous study. According to (EQN. 3), the signal magnitude dynamic response, $M_{rise}(t)$, during application of ARF (see FIG. 1) can be described as:

$$M_{rise}(t) = M_{satu} - (M_{satu} - M_{init}) \times e^{-\frac{t}{\tau_{rise}}} \quad \text{(EQN. 5)}$$

where $M_{init}$ is the initial signal magnitude before the application of ARF pulses; $M_{satu}$ is the saturated signal magnitude after applying ARF for a sufficiently long time (i.e. after reaching steady-state); and $\tau_{rise}$ is the time constant. $M_{init}$ and $M_{satu}$ are proportional to $N_{AMB}^{ON}$ and $$\frac{k_+^{ON}}{k_-^{ON}}(N_{FMB}^{ON}d)N_B,$$

respectively. $\tau_{rise}$ equals to $1/k_-^{ON}$. After cessation of ARF, according to (EQN. 4), the decay section of signal magnitude curve, $M_{decay}(t)$, can be described as:

$$M_{decay}(t) = M_{resid} - (M_{resid} - M_{max}) \times e^{-\frac{t}{\tau_{decay}}} \quad \text{(EQN. 6)}$$

where $M_{max}$ is the signal magnitude immediately after cessation of ARF; $M_{resid}$ is the residual signal magnitude after reaching steady-state; and $\tau_{decay}$ is the time constant. $M_{max}$ approaches $M_{satu}$ as the time of ARF application goes to infinity. $M_{max}$ and $M_{resid}$ are proportional to $N_{AMB}^{OFF}$ and $$\frac{k_+^{OFF}}{k_-^{OFF}}(N_{FMB}^{OFF}d)N_B,$$

respectively. $\tau_{decay}$ equals to $1/k_-^{OFF}$.

FIG. 1 illustrates a representative example of an ultrasound signal magnitude curve 20 as determined by EQNS. (5) and (6) in response to a modulated ARF input 22 (see also FIG. 3). The graph plots a time series 24 of ultrasound signal magnitude against time developed from received echo data. Corresponding signal magnitude parameters of the response are labeled as: an initial signal magnitude parameter 26 ($M_{init}$ parameter 26), a time constant of rise parameter 28 ($\tau_{rise}$ 28 parameter—a function of the signal rise time), a maximum signal magnitude parameter 30 ($M_{max}$ parameter 30), a time constant of decay parameter 32 ($\tau_{decay}$ parameter 32–a function of the signal fall time), a saturated signal magnitude parameter 34 ($M_{satu}$ parameter 34), and a residual signal magnitude parameter 36 ($M_{resid}$ parameter 36). The ultrasound signal magnitude was assumed to be directly proportional to microbubble concentration of adherent microbubbles along a bottom vessel wall. The modulated ARF input 22 can include a first temporal period 23 that includes ARF pulses (ARF "on") and a second temporal period 25 that does not include ARF pulses (ARF "off").

In this disclosure data is described as "averaged", but other methods of determining a central tendency can also be used such as determining a median, determining a mode, or other central tendency. In this disclosure, the modulated ARF input 22 is described as having a period of time where there is no applied ARF ($M_{init}$ parameter 26), followed by a period of time having ARF applied (ending at $M_{max}$ parameter 30), followed by a period of time having no ARF applied. The present inventors have contemplated other configurations of modulated ARF input 22, such as having more than one period of applied ARF, without changing the intent of this disclosure.

Experimental Materials and Methods

Figure 2:
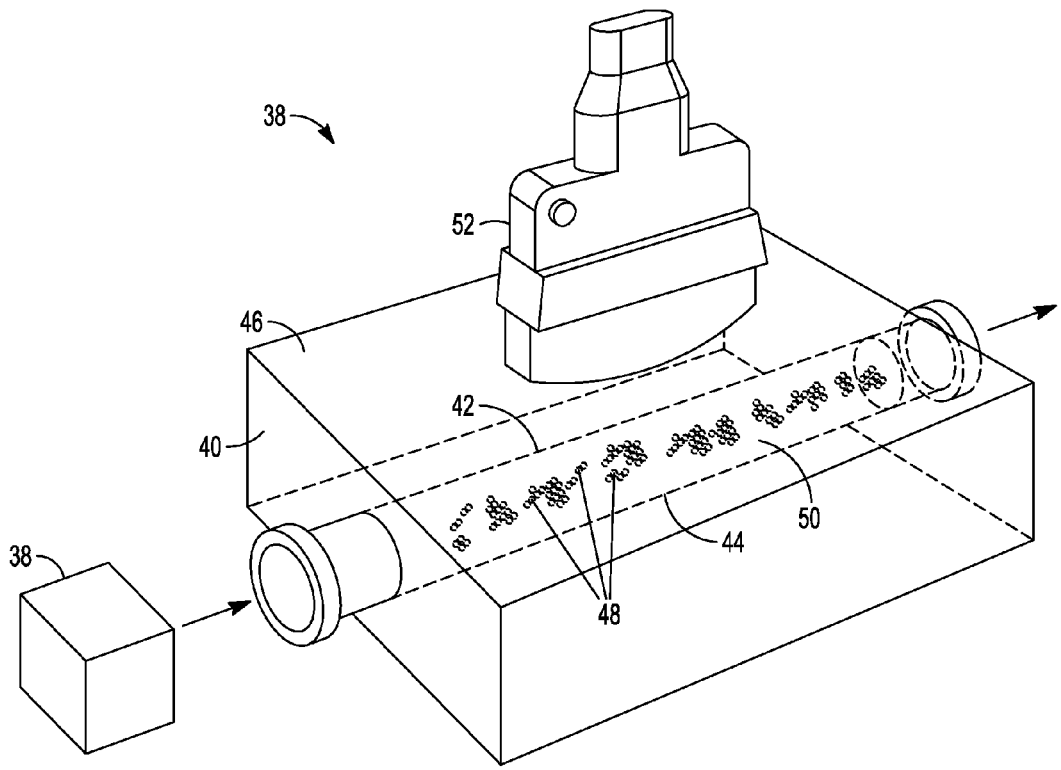
FIG. 2 illustrates an example of an experimental in vitro set up, in accordance with at least one example of the present subject matter.

FIG. 2 illustrates an example of an experimental in vitro set up 38 the present inventors established that tested the equations disclosed above. It should be recognized that the present inventors have contemplated uses of the present invention as a diagnostic method or device performed or used in laboratory fixtures as well as a diagnostic method or device performed or used on living humans or animals (in vivo). Flow phantoms 40 with fluid channels 42 were used to mimic the elastic and acoustic properties of tissue. 6.1% (w/w) gelatin (Type B, Fisher Scientific, Pittsburgh, Pa.), 2.2% (w/w) agar (Acros Organics, Geel, Belgium) and 1.8% (w/w) graphite (<20 μm, Sigma-Aldrich, St. Louis, Mo.) were dissolved in boiling water and then poured into a custom designed phantom holder (e.g. flow phantom) (Applied Rapid Technologies, Fredericksburg, Va.) at a temperature of 75° C. (FIG. 2). Borosilicate glass rods (Mc-Master-Carr, Robbinsville, N.J.) with diameter of 4 mm were placed horizontally inside the flow phantom 40 to mold fluid channels 42. A bottom channel wall 44 of the embedded fluid channel 42 was approximately 8 mm from an imaging surface 46 of the flow phantom 40. To minimize the effects of inner fluid channel surface roughness on microbubble binding, all inner surfaces were examined optically and then observed under ultrasound to verify the presence of a smooth, specular reflecting, phantom wall. Targeted fluid channels were created using an incubation with 50 μg mL-1 streptavidin (AnaSpec, Fremont, Calif.) solution for 12 h followed by another incubation with 5% (w/w) bovine serum albumin (BSA, Sigma-Aldrich, St. Louis, Mo.) for 1 h. Control fluid channels were incubated with 5% (w/w) BSA alone for 12 h. In this disclosure, each fluid channel was used for one trial only (3 min of flowing microbubble solution).

The targeted fluid channels allowed for specific binding adherence of targeted microbubbles 48, while the control fluid channels would only allow non-specific binding adherence, because there were no receptor sites to specifically receive the targeted microbubbles 48 in the control fluid channels.

Biotinylated lipid shelled microbubbles (mean diameter approximate 2.2 µm), synthesized in-house using existing methods were used as targeted microbubbles 48 to specifically adhere to the streptavidin in the targeted channel. The present inventors have contemplated using any type of ligand/receptor binding platform without changing the intent of this disclosure. The biotinylated lipid shelled microbubbles were diluted in 0.9% Sodium Chloride Irrigation, USP (Baxter Healthcare Corporation, Deerfield, Ill.) at concentrations of 0.1, 0.5, and 2.0 (106 mL-1). Empirically, it has been shown that it is preferable to use acoustic radiation force for pushing those microbubbles at a transmit frequency of approximate 4 MHz. BSA at 0.5% (w/w) was added to a microbubble solution 50 to further prevent non-specific adhesion as shown by a previous study. To maintain consistent microbubble concentration, a Coulter counter (Coulter Multisizer 3, Beckman Coulter Inc., Brea, Calif.) was used to determine the microbubble concentration immediately before experiments; and fresh microbubble solution 50 was prepared every 10 min during experiments.

An ultrasound transducer 52 (described also in FIG. 10) used in these experiments was placed perpendicular to the bottom channel wall 44, which was located at a depth of 14 mm. Experiments were performed by injecting the microbubble solution 50 through the fluid channels 42 at flow velocities of 2, 6, and 10 cm s−1 (i.e. flow rates of 15.1, 45.2, and 75.4 mL min-1, respectively) using a syringe pump 54 (PHD 2000, Harvard Apparatus, Holliston, Mass.). The proposed flow velocities (2-10 cm s−1) and vessel diameter (4 mm) in this disclosure represented typical averaged flow velocities and vessel diameters of large human blood vessels (e.g. brachial artery, averaged flow velocity≈9 cm s−1, averaged arterial diameter≈4 mm). Constant flow velocities and microbubble concentrations were maintained for 3 min while custom designed beam sequences (e.g. transmitted pulse sequences described below) were performed. Raw radiofrequency (RF) echo data was obtained for analysis of the adherent microbubble signal magnitude.

Figure 3:
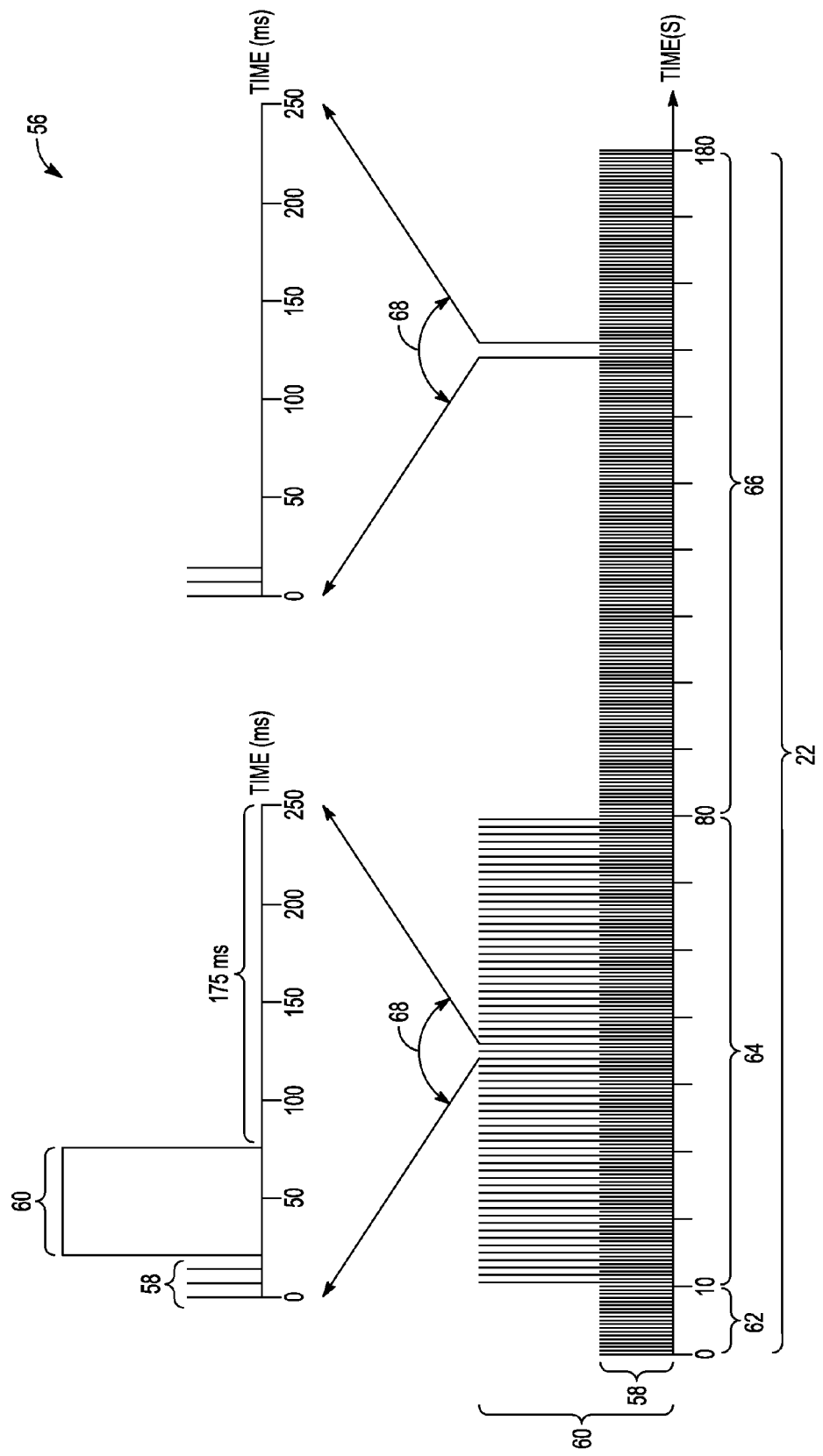
FIG. 3 illustrates an example diagram of a transmitted pulse sequence having modulated ARF, in accordance with at least one example of the present subject matter.

FIG. 3 illustrates an example diagram of a transmitted pulse sequence 56 for a modulated ARF input 22. The transmitted pulse sequence 56 can include imaging pulses 58 and ARF pulses 60. The imaging pulses 58 are shown in blue and the ARF pulses 60 are shown in red. The amplitudes of imaging and ARF pulses 58, 60 are not to scale.

Custom pulse sequences were programmed on a Verasonics ultrasound scanner (Verasonics, Inc., Redmond, Wash.) equipped with an ATL L12-5 38 mm linear array transducer (Philips Healthcare, Andover, Mass.). For each experimental trial, the sequence collected acoustic echo data continuously for 180 s at a frame rate of 4 Hz. The transmitted pulse sequence 56 can be divided into three sections: an initial temporal period 62, an intermediate temporal period 64, and a final temporal period 66. For each frame period 68 (250 ms), three plane wave imaging pulses 58 with a spacing of 200 µs were fired consecutively to obtain the acoustic echo data 70 required to form one image frame 72 (see FIG. 4B). These three consecutive imaging pulses 58 were identical. There was no amplitude or phase modulation performed. Focused A-lines were constructed by standard plane wave dynamic receive focusing methods. From t=10 s to 80 s, additional ARF pulses 60 were inserted in each frame period 68 following the imaging pulses 58 to increase microbubble binding efficiency along the bottom channel wall as has been shown in a previous approach. The time interval between the ARF pulses 60 and the following imaging pulses 58 from the next frame was 175 ms—a sufficiently long time period for the system power supply to transition from a high voltage profile (5 V, ARF pulses) to a low voltage profile (1.6 V, imaging pulses). The transmitted pulse sequence 56 is an example and pulse times for the initial temporal period 62, the intermediate temporal period 64, and the final temporal period 66 can be varied to suit a particular imaging application. The frame period 68 disclosed above, is an example and frame periods 68 including different numbers of imaging pulses, time periods, spacings, ARF periods, and signal magnitudes are contemplated by the inventors without changing the nature of this disclosure.

It was known a priori that adherent targeted microbubbles 48 would accumulate along the bottom channel wall 44 (see FIG. 2) under the ARF pulses 60 as has been confirmed by fluorescent microscopy in previous studies. Although the channel wall is described as the "bottom channel wall" the present inventors have contemplated that an applied ARF would tend to cause microbubbles to accumulate in a direction away from the propagation of the ARF and the orientation of the fluid channel and the channel wall onto which adherent microbubbles accumulate is a matter of positioning of the transducer relative to the fluid channel and this disclosure is not limited to a particular wall of the fluid channel. Average pulse repetition frequencies (PRF) of ARF pulses were chosen at 0.5, 2.5, and 5 kHz. A detailed list of parameters used for imaging and ARF pulses are provided in Table 1. In order to minimize possible effects of imaging pulses 58 on microbubble binding, the voltage applied to the ultrasound transducer 52 (see FIG. 2) during imaging was maintained at the lowest programmable limit of the scanner, which gave a low mechanical index (MI) of 0.006 as confirmed with hydrophone measurements. In addition, the intensity of ARF pulses 60 was optimized to provide sufficient pushing pressure (110.3 kPa) while maintaining a low MI of 0.05, which are below the published limits at which bursting has been shown to occur.

Consequently, the transmitted pulse sequence 56 was divided into three sections, an initial temporal period 62 with 10 s of imaging (0 s≤t≤10 s) having not including ARF (ARF off), an intermediate temporal period 64 having 70 of imaging plus ARF applied (10 s≤t≤80 s), and a final temporal period 66 of 100 s of imaging (80 s≤t≤180 s) with not including ARF (ARF off). FIG. 1 illustrates an example graph of such a pulse sequence showing the baseline, rise, and decay of adherent microbubble concentration along the bottom channel wall.

TABLE 1

Acoustic parameters used in various experiments

| Pulse type | Imaging pulse | ARF pulse |
|---|---|---|
| Detail | Plane wave | Plane wave |
| | Center frequency = 4.5 MHz | Center frequency = 4.5 MHz |
| | Pulse length = 1 cycle | Pulse length = 15 cycles |
| | PRF[a] = 12 Hz | PRF = 0.5, 2.5, 5 kHz |
| | Peak-negative pressure = 12.3 kPa | Peak-negative pressure = 110.3 kPa |
| | MI[b] = 0.006 | MI = 0.05 |
| | Frame rate = 4 Hz[c] | |

[a]Average pulse repetition frequency
[b]Mechanical index
[c]Echo data from three consecutive imaging pulses was used to form one image. Frame rate = PRF/3 = 4 Hz.

Experiments were designed by the present inventors to test the effects of flow velocity, microbubble concentration, and ARF intensity on adherent microbubble signal magnitude curves. Flow and acoustic parameters of different groups are listed in Table 2. The $G_{Ref}$ label used throughout this disclosure represents the reference group, while $G_{v1}$ and $G_{v2}$ represent groups with a lower and a higher flow velocity compared to the $G_{Ref}$ group, respectively. $G_{C1}$ and $G_{C2}$ represent groups with a lower and a higher microbubble concentration relative to the $G_{Ref}$ group. $G_{PRF1}$ and $G_{PRF2}$ were two groups with lower PRF of ARF pulses compared to the $G_{Ref}$ group, and therefore a lower time averaged ARF intensity. For each group, experiments from 10 targeted and 10 control channels were performed. Each experiment was performed in a unique phantom channel in order to eliminate measurement bias that could result from phantom-to-phantom or batch-to-batch microbubble variations.

TABLE 2

Flow and acoustic parameters for different groups of experiments

| Parameter | Group name | | | | | | |
|---|---|---|---|---|---|---|---|
| | $G_{Ref}$ | $G_{v1}$ | $G_{v2}$ | $G_{C1}$ | $G_{C2}$ | $G_{PRF1}$ | $G_{PRF2}$ |
| $v_{flow}{}^a$ (cm s$^{-1}$) | 6.0 | 2.0 | 10 | 6.0 | 6.0 | 6.0 | 6.0 |
| $C_{MB}{}^b$ (10$^6$ mL$^{-1}$) | 0.5 | 0.5 | 0.5 | 0.1 | 2.0 | 0.5 | 0.5 |
| PRF (kHz) | 5.0 | 5.0 | 5.0 | 5.0 | 5.0 | 0.5 | 2.5 |

$^a$Flow velocity
$^b$Microbubble concentration

Quantitative analysis was performed on focused acoustic echo data from 720 consecutive image frames. All analysis was performed in MATLAB (Mathworks, Natick, Mass.). For each trial, signal magnitude curves (M(t), 0 ≤t≤180 s) were obtained by calculating the average signal magnitude (after envelope detection of focused echo data) from regions of adherent microbubbles over time within a region of interest (ROI). The ROI was located at the center of the bottom channel wall and possessed a depth span of 0.2 mm and a lateral width of 2 mm. Although the region of interest was finitely described for the experiments, the inventors have contemplated regions of interest of larger and smaller sizes at other locations in a fluid channel. The following calculation was used to compute the averaged signal magnitude over the ROI:

$$M = \frac{1}{N_1 \times N_2}\left(\sum_{j=1}^{N_2}\sum_{i=1}^{N_1}\sqrt{I(i,j)^2 + Q(i,j)^2}\right) \quad \text{(EQN. 7)}$$

where I(i, j) and Q(i, j) are the real (in-phase) and imaginary (quadrature) components of the focused echo data within the ROI (dimension: N1×N2), respectively.

The depth of the ROI along the bottom channel wall was determined with an automated program that detected the location of maximum average signal magnitude over all image frames. The ROI spanned 10 consecutive laterally adjacent A-lines to increase measurement signal-to-noise. For each set of flow and acoustic conditions, 10 signal magnitude curves were calculated from 10 trials.

As described above in FIG. 1, the initial signal magnitude parameter 26 ($M_{init}$), saturated signal magnitude 34 ($M_{satu}$), maximum signal magnitude 30 ($M_{max}$), residual signal magnitude 36 ($M_{resid}$), time constant of rise 28 ($\tau_{rise}$) and time constant of decay 32 ($\tau_{decay}$) were the parameters used to characterize the signal magnitude curves of adherent microbubbles under the custom designed pulse sequences.

For signal magnitude curves (both from averaged and single trial), the second section (M(t), 10 s≤t≤80 s) and the third section (M(t), 80 s≤t≤180 s) were used to fit (EQN. 5) and (EQN. 6), respectively, using the Curve Fitting Toolbox in MATLAB. Adjusted-R2 values were used to evaluate the fitting performance. Parameters of $M_{satu}$, $\tau_{rise}$, $M_{resid}$ and $\tau_{decay}$ were obtained from curve fitting. The $M_{init}$ parameter was obtained from the signal magnitude curve at t=5 s. The $M_{max}$ parameter was the maximum signal magnitude value during the entire 180 s period. For each set of flow and acoustic conditions, the fitting process was repeated over 10 trials. Thereafter, Student's t-tests were performed on those parameters among different sets of flow and acoustic conditions. Differences were considered statistical significant only if the calculated p-value was less than 0.05.

An additional signal magnitude curve parameter, ratio of residual to saturation signals ($R_{resid}$), was studied to assess its ability to detect targeted adhesion. The parameter is defined as:

$$R_{resid} = \left(\frac{M_{resid} - M_{init}}{M_{satu} - M_{init}}\right) \times 100\% \quad \text{(EQN. 8)}$$

where $M_{init}$ and $M_{resid}$ are measured directly from the signal magnitude curve, M(t), at t=5 s and t=180 s, respectively; $M_{satu}$ is the saturated signal magnitude after reaching steady-state. According to the model in (EQN. 5), the $M_{satu}$ parameter corresponds to full saturation of adherent microbubbles (both specific and non-specific binding) and the $M_{init}$ parameter corresponds to background signal in absence of adherent microbubbles. According to the model in (EQN. 6), only targeted ligand-receptor bound microbubbles remain after cessation of ARF. These targeted ligand-receptor bound microbubbles are targeted microbubbles that have specifically bound to target receptors in the channel wall. The concentration of remaining microbubbles can be quantified by the $M_{resid}$ parameter, which is bounded by $M_{init}$ (lower bound) and $M_{satu}$ (upper bound). Therefore, the $R_{resid}$ value can represent the percentage of these bounds that is spanned by the $M_{resid}$ quantity.

Returning to FIG. 1, and to describe EQN. 8 in other words, the $M_{init}$ parameter 26 can be considered background signal and can be subtracted from the $M_{satu}$ parameter 34 to correspond to a to full saturation of adherent microbubbles (both specific and non-specific binding) at the bottom channel wall 44 (see FIG. 2) in the region of interest 87 (see FIG. 4C) less the background noise of the $M_{init}$ parameter 26. When ARF is turned off, targeted microbubbles that are not specifically bound to the channel wall can be removed from the region of interest 87 by flow shear forces because they have a much weaker adherence to the channel wall 44 and are no longer pushed towards the channel wall by the ARF. After a sufficient decay time, a stable residual signal magnitude parameter 36 ($M_{resid}$ parameter 36) can be detected. Subtracting the background signal of the $M_{init}$ parameter 26 from the $M_{resid}$ parameter 36 can provide a quantity corresponding to the number of specifically bound targeted microbubbles. EQN. 8 compares these quantities and expresses as a percentage. Because $R_{resid}$ is not dependent on absolute signal magnitude levels, it is proposed in this disclosure that it can provide more reliable detection of targeted adhesion independent of control measurements.

Experimental Results

Figure 4A:
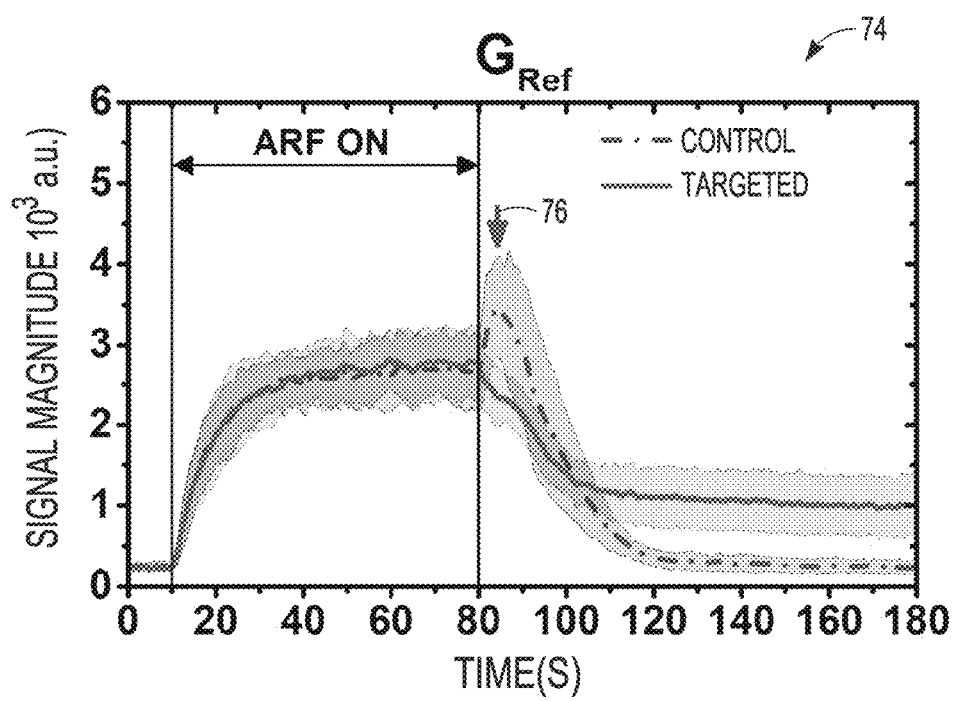
FIG. 4A is a graph illustrating averaged signal magnitude curves for a control channel and a targeted channel of a reference group, in accordance with at least one example of the present subject matter.

The effects of control and targeted channels on signal magnitude curves are disclosed below. FIG. 4A is a graph illustrating averaged signal magnitude curves versus time 74 for a control channel and a targeted channel of a reference group. Blue dash-dot and red solid lines indicate the mean values from 10 trials. Light color shadows indicate the corresponding error bars at the range of [mean±standard deviation]. The blue arrow shows a control peak 76 of the signal magnitude curve in control channel at t=84.50 s.

FIGS. 4B-4C illustrates B-mode images 78 of acoustic echo data 70 displayed at 50 dB dynamic range that show the channel lumen of control channels (FIG. 4B) and targeted channels (FIG. 4C) at different times: control, t=5.00 s 79; targeted, t=5.00 s 80; control, t=80.00 s 81; targeted, t=80.00 s 82; control, t=84.50 s (control peak) 83; targeted, t=84.50 s 84; control, t=180.00 s 85; targeted, t=180.00 s 86. The windows indicate a region of interest 87 (ROI) with dimensions of 2 mm×0.2 mm. Microbubble solution flowed from left to right at a velocity of 6.0 cm s$^{-1}$. It is contemplated by the inventors that a region of interest 87 can be located in an in vivo vascular system as well as in flow phantoms and can be set to any desired size, depth, or location.

Representative signal magnitude curves observed during the modulated ARF pulse sequence are illustrated in FIG. 4A (default imaging conditions listed as the $G_{Ref}$ group in Table 2). The signal magnitude curves represent the average over 10 trials for both control and targeted experiments. In both curves, during the first 10 s period with no application of ARF, there was no significant change of signal magnitude (p>0.2, n=10). During the next 70 s period, with application of ARF, the signal magnitude for both control and targeted channels exponentially approached a steady-state magnitude in excellent agreement with the proposed model (adjusted-$R^2$ value of 0.99 to fit EQN. 5). During the last 100 s period after cessation of ARF, the signal magnitude of targeted channels exhibited an exponential decay to a residual level, again in excellent agreement with the proposed model (adjusted-$R^2$ value of 0.97 to fit EQN. 6). However, in the control channels, an immediate increase in signal magnitude (control peak 76) was observed after cessation of ARF. As will be further illustrated below, the control peak 76 observation was consistent across a wide of range of flow rates, microbubble concentrations, and ARF investigated in this disclosure. After reaching the control peak (t=84.50 s), the control curve demonstrated the same exponential decay to a residual level as observed in the targeted example (adjusted-$R^2$ value of 0.96 to fit EQN. 6).

Figure 5A:
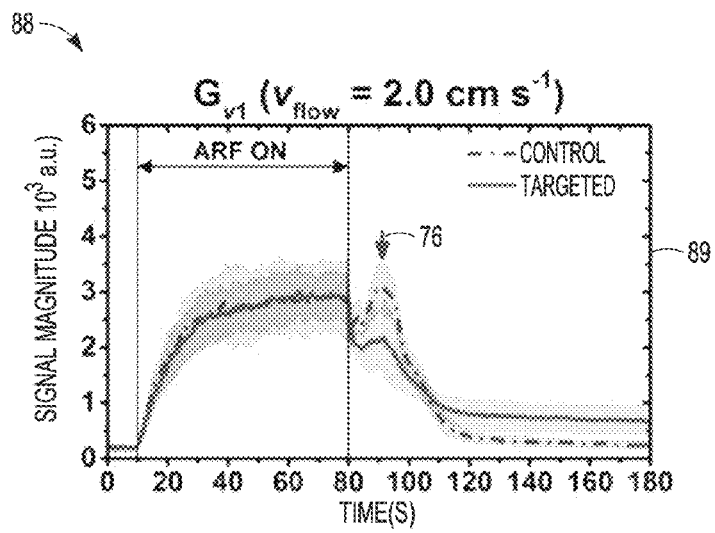
FIG. 5A is a graph illustrating averaged signal magnitude curves of control and targeted channels at the $G_{v1}$ flow condition (Table 2), in accordance with at least one example of the present subject matter.
Figure 5B:
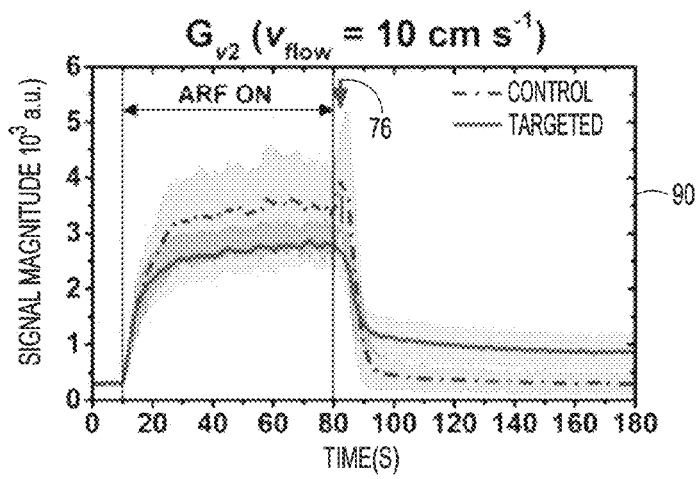
FIG. 5B is a graph illustrating averaged signal magnitude curves of control and targeted channels at the $G_{v2}$ flow condition (Table 2), in accordance with at least one example of the present subject matter.
Figure 5C:
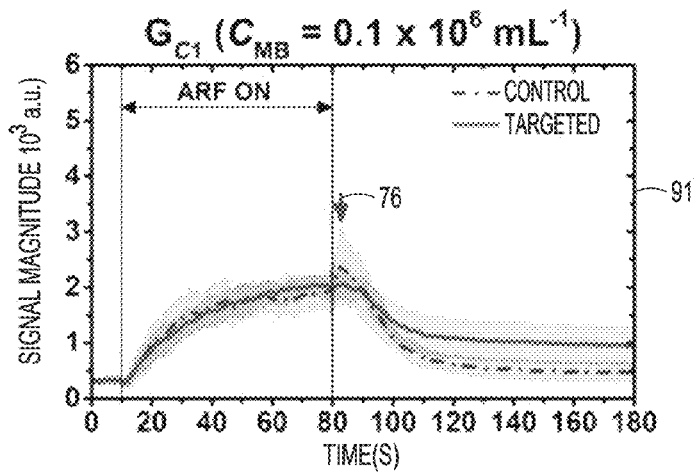
FIG. 5C is a graph illustrating averaged signal magnitude curves of control and targeted channels at the $G_{C1}$ concentration condition (Table 2), in accordance with at least one example of the present subject matter.
Figure 5D:
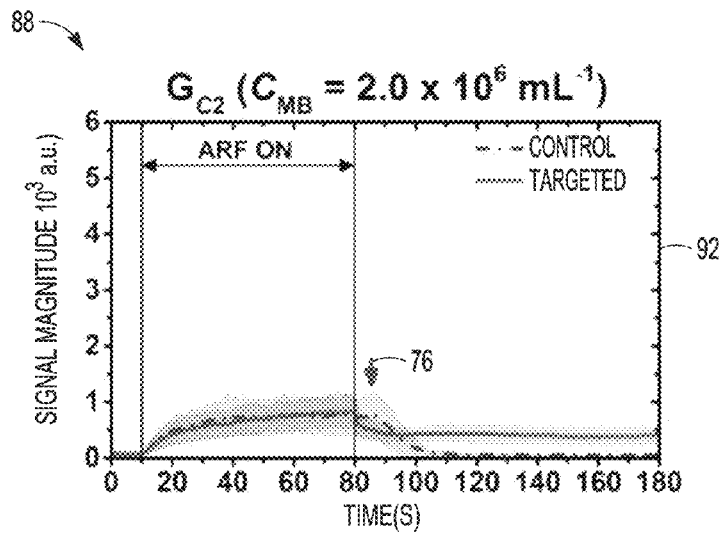
FIG. 5D is a graph illustrating averaged signal magnitude curves of control and targeted channels at the $G_{C2}$ concentration condition (Table 2), in accordance with at least one example of the present subject matter.
Figure 5E:
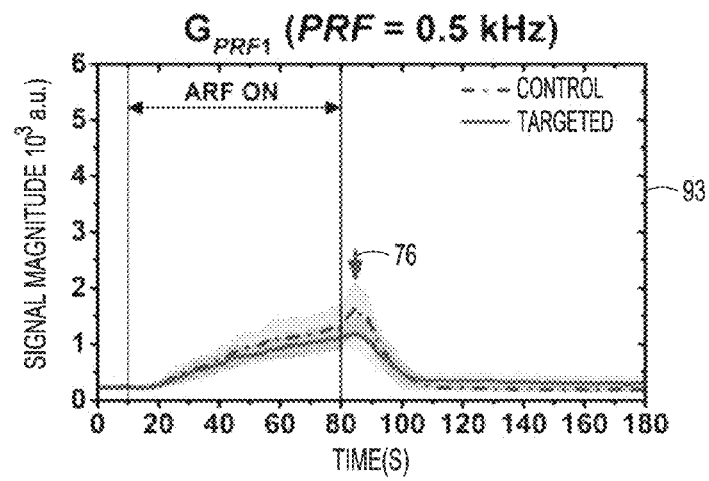
FIG. 5E is a graph illustrating averaged signal magnitude curves of control and targeted channels at the $G_{PRF1}$ acoustic intensity condition (Table 2), in accordance with at least one example of the present subject matter.
Figure 5F:
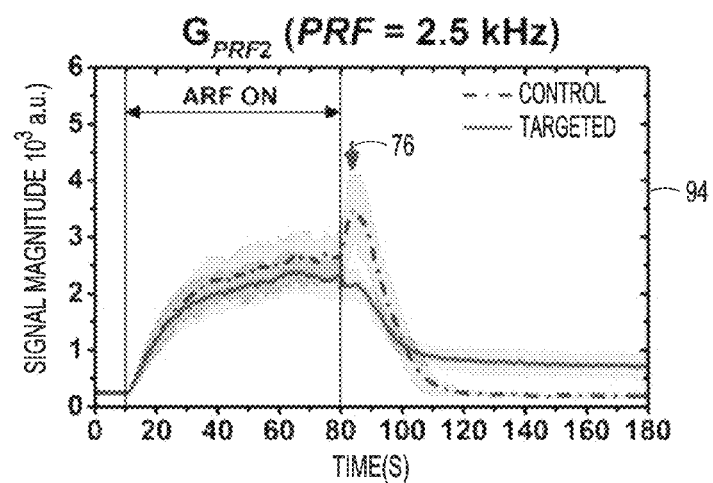
FIG. 5F is a graph illustrating averaged signal magnitude curves of control and targeted channels at the $G_{PRF2}$ acoustic intensity condition (Table 2), in accordance with at least one example of the present subject matter.

FIGS. 5A-5F include charts illustrating averaged signal magnitude curves 88 for control and targeted channels for flow rate, concentration, and acoustic conditions of groups listed in Table 2. Blue dash-dot and red solid lines indicate the mean values from 10 trials. Light color shadows indicate the corresponding error bars at the range of [mean±standard deviation]. Blue arrows show the control peaks 76 of signal magnitude curves of the control channel at the different groups. FIG. 5A illustrates the $G_{v1}$ averaged signal magnitude curve 89 in which the flow velocity was maintained at 2.0 cm s$^{-1}$. FIG. 5B illustrates the $G_{v2}$ averaged signal magnitude curve 90 in which the flow velocity was maintained at 10.0 cm s$^{-1}$. FIG. 5C illustrates the $G_{C1}$ averaged signal magnitude curve 91 in which the concentration of the microbubble solution was maintained at 0.1×10$^6$ mL$^{-1}$. FIG. 5D illustrates the $G_{C2}$ averaged signal magnitude curve 92 in which the concentration of the microbubble solution was maintained at 2.0×10$^6$ mL$^{-1}$. FIG. 5E illustrates the $G_{PRF1}$ averaged signal magnitude curve 93 in which the ARF intensity (pulse repetition frequencies PRF) was maintained at 0.5 kHz. FIG. 5F illustrates the $G_{PRF1}$ averaged signal magnitude curve 93 in which the ARF intensity (pulse repetition frequencies PRF) was maintained at 2.5 kHz.

For the six different groups in FIGS. 5A-F: the region of the signal magnitude curve (both control and targeted) with application of ARF (10 s≤t≤80 s) fit EQN. 5 with a minimum adjusted-$R^2$ value of 0.95. The control peak 76 of signal magnitude curves for control channels was observed in all six groups at different times ($G_{v1}$, t=90.75 s; $G_{v2}$, t=82.50 s; $G_{C1}$, t=83.00 s; $G_{C2}$, t=85.50 s; $G_{PRF1}$, t=85.00 s; $G_{PRF2}$, t=84.50 s). Hence, for control channels, the curve fit following application of ARF to EQN. 6 started from the time of the control peak 76 to the end of the signal magnitude curve (t=180 s); for targeted channels, the range was from 80 s to 180 s. The minimum adjusted-$R^2$ value from these experiments was 0.92 except for the $G_{C2}$ averaged signal magnitude curve 92 (adjusted-$R^2$=0.89 for control and 0.71 for targeted channels).

Figure 6A:
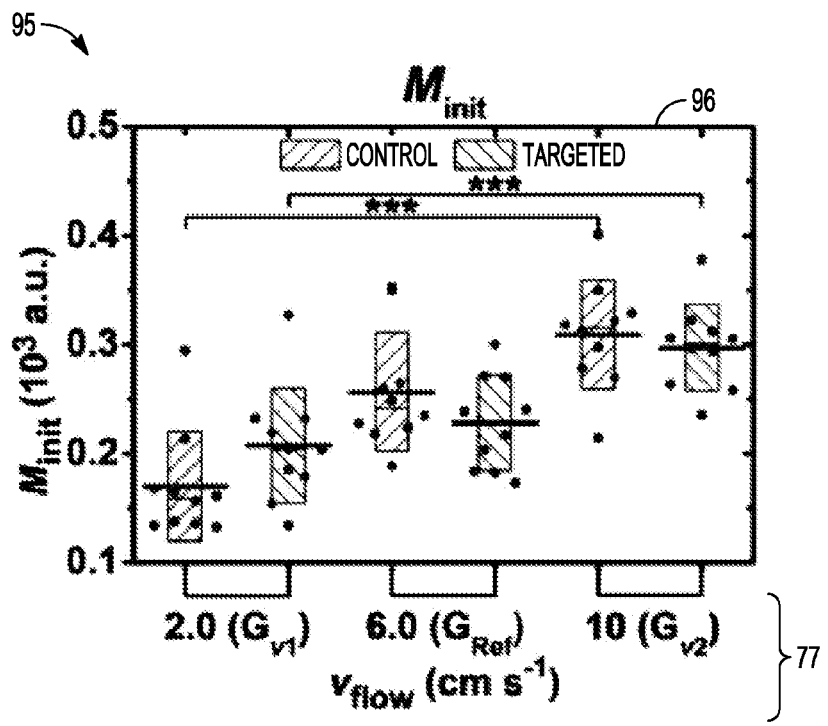
FIG. 6A is a chart illustrating effects of flow velocities on an initial signal magnitude parameter ($M_{init}$ parameter) extracted from control and targeted signal magnitude curves during modulated ARF experiments, in accordance with at least one example of the present subject matter.
Figure 6B:
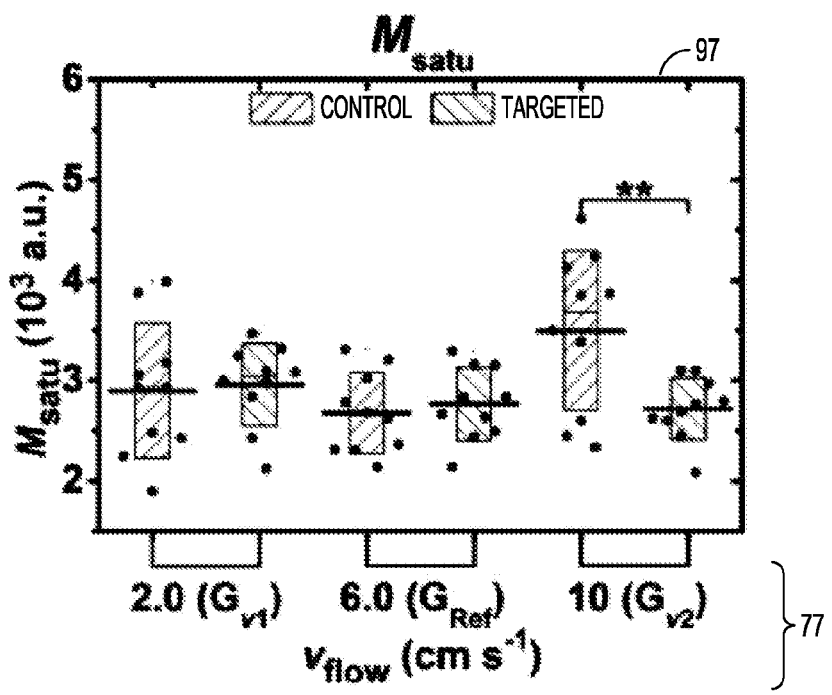
FIG. 6B is a chart illustrating effects of flow velocities on a saturated signal magnitude parameter ($M_{satu}$ parameter) extracted from control and targeted signal magnitude curves during modulated ARF experiments, in accordance with at least one example of the present subject matter.
Figure 6C:
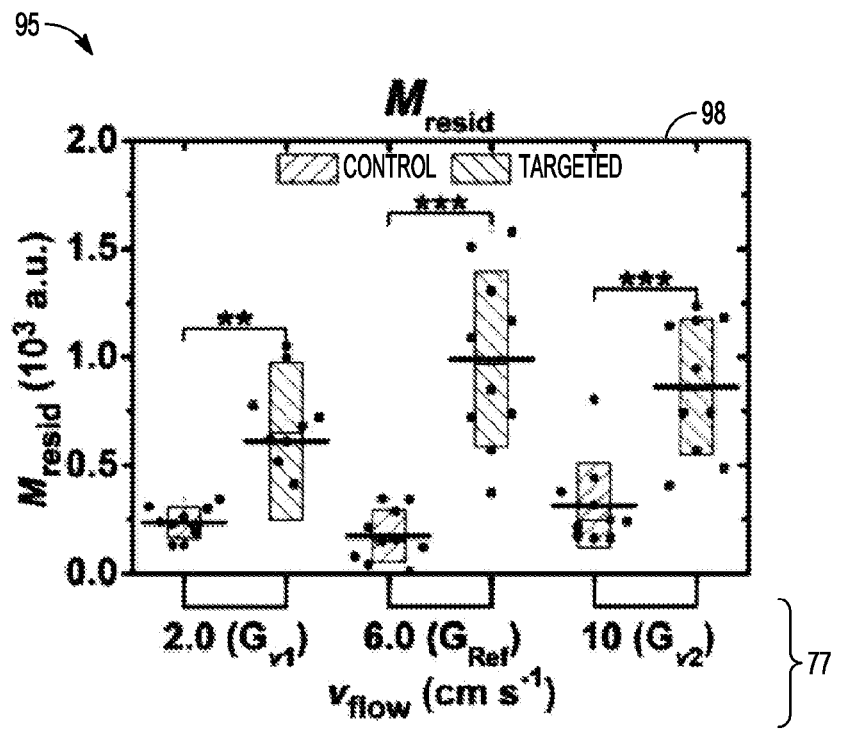
FIG. 6C is a chart illustrating effects of flow velocities on a residual signal magnitude parameter ($M_{resid}$ parameter) extracted from control and targeted signal magnitude curves during modulated ARF experiments, in accordance with at least one example of the present subject matter.
Figure 6D:
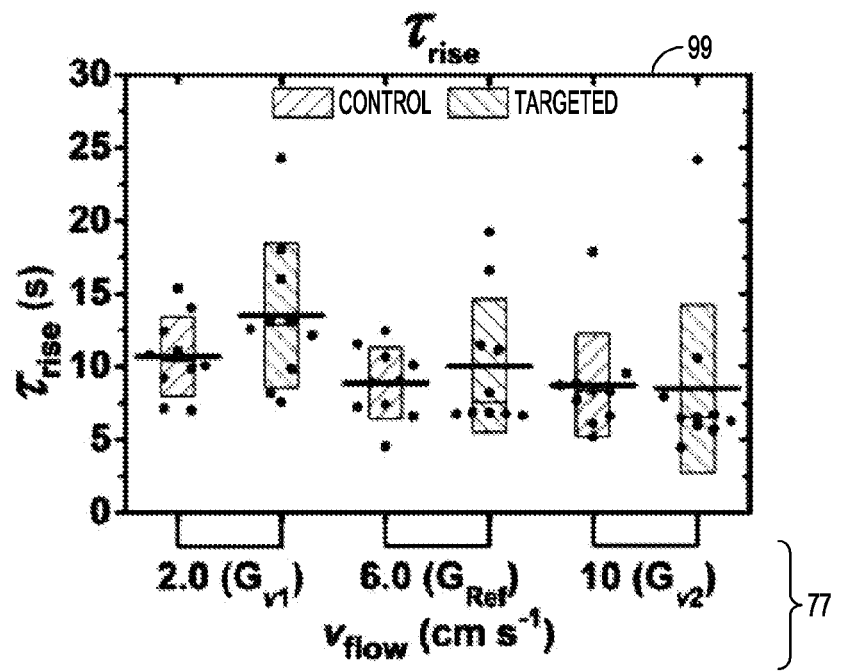
FIG. 6D is a chart illustrating effects of flow velocities on a time constant of rise parameter ($\tau_{rise}$ parameter) extracted from control and targeted signal magnitude curves during modulated ARF experiments, in accordance with at least one example of the present subject matter.
Figure 6E:
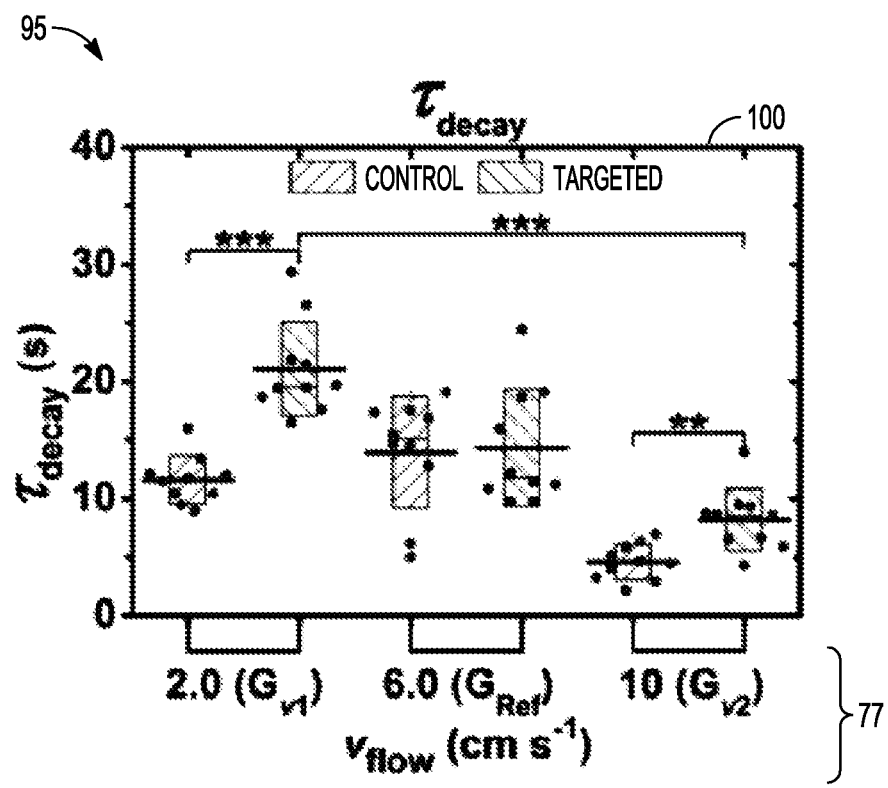
FIG. 6E is a chart illustrating effects of flow velocities on a time constant of decay parameter ($\tau_{decay}$ parameter) extracted from control and targeted signal magnitude curves during modulated ARF experiments, in accordance with at least one example of the present subject matter.

FIGS. 6A-E include bar charts illustrating the effects of flow velocities 77 on parameters extracted from signal magnitude curves during modulated ARF experiments 95. The parameters are: $M_{init}$ parameter 26, $M_{satu}$ parameter 34, $M_{resid}$ parameter 36, $\tau_{rise}$ parameter 28, and $\tau_{decay}$ parameter 32 of signal magnitude curves for groups of $G_{v1}$, $G_{Ref}$, and $G_{v2}$. FIG. 6A illustrates the effects of flow velocities 77 on the $M_{init}$ parameter 26: $M_{init}$ v. flow 96. FIG. 6B illustrates the effects of flow velocities 77 on the $M_{satu}$ parameter 34: $M_{satu}$ v. flow 97. FIG. 6C illustrates the effects of flow velocities 77 on the $M_{resid}$ parameter 36: $M_{resid}$ v. flow 98. FIG. 6D illustrates the effects of flow velocities 77 on the $\tau_{rise}$ parameter 28: $\tau_{rise}$ v. flow 99. FIG. 6E illustrates the effects of flow velocities 77 on the $\tau_{decay}$ parameter 32: $\tau_{decay}$ v. flow 100. The bar charts show the parameters averaged from 10 trials at different flow velocities and fluid channels (e.g. control and targeted). In the charts, boxes show the range [mean±standard deviation]. Black lines located at the center of the boxes show the corresponding mean value. Raw data from 10 trials are shown as solid dots overlaying the corresponding boxes. For Student's t-test, *: p<0.05, : p<0.01, *: p<0.001, n=10. According to Table 2, flow velocity 77 was the only parameter varied among these three groups. In FIG. 6A, the $M_{init}$ parameter 26 increased monotonically with flow velocity 77, with a significant difference between the minimum and maximum $M_{init}$<0.001, n=10) ($M_{init}$ parameter 26). In FIG. 6B, the $G_{v2}$ group, the $M_{satu}$ parameter 34 for the control channel was significantly higher than that of the targeted channel (p<0.01, n=10). In FIG. 6C, the $M_{resid}$ parameter 36 of targeted channel was significantly higher than that of control for all three groups of $G_{v1}$, $G_{Ref}$, and $G_{v2}$ (p<0.01, p<0.001, and p<0.001, correspondingly; n=10). In FIG. 6D, there was no significant difference of the $\tau_{rise}$ parameter 28 between control and targeted channels for all three groups. In FIG. 6E, the $\tau_{decay}$ parameter 32 of targeted channel was significantly higher than that of control channels in groups $G_{v1}$ and $G_{v2}$ (p<0.001, and p<0.01, correspondingly; n=10). In addition, the $\tau_{decay}$ parameter 32 of targeted channels decreased monotonically with flow velocity, with a significant difference observed between the minimum and maximum $\tau_{decay}$ (p<0.001, n=10).

Figure 7A:
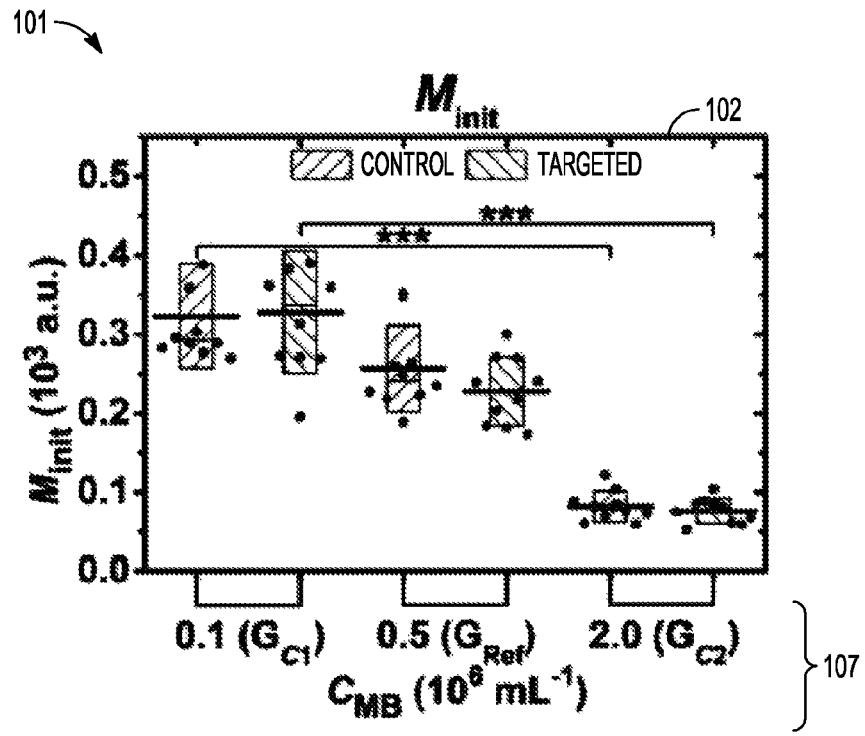
FIG. 7A is a chart illustrating effects of microbubble concentration on the initial signal magnitude parameter ($M_{init}$ parameter) extracted from control and targeted signal magnitude curves during modulated ARF experiments, in accordance with at least one example of the present subject matter.
Figure 7B:
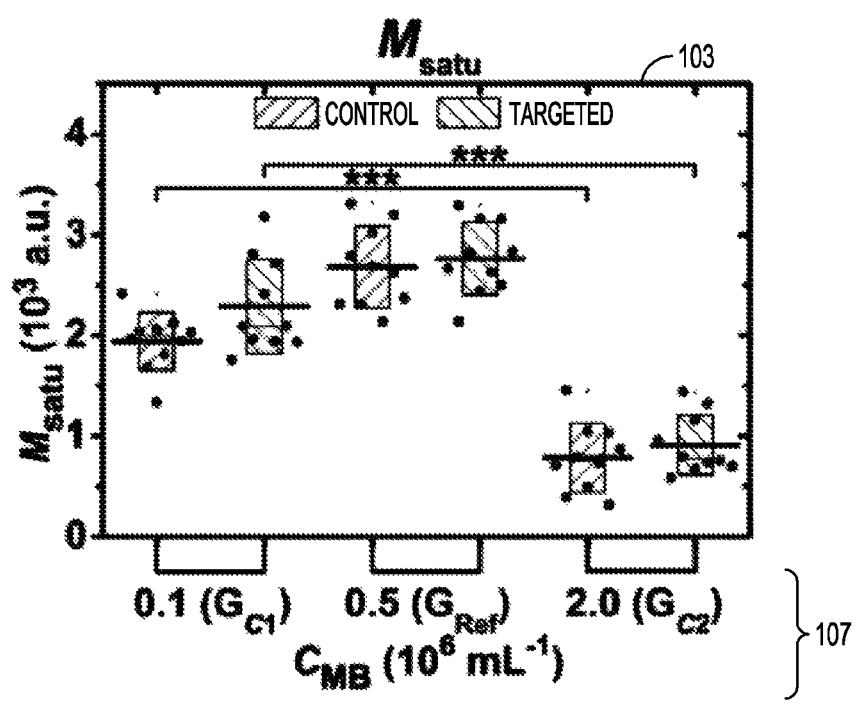
FIG. 7B is a chart illustrating effects of microbubble concentration on the saturated signal magnitude parameter ($M_{satu}$ parameter) extracted from control and targeted signal magnitude curves during modulated ARF experiments, in accordance with at least one example of the present subject matter.
Figure 7C:
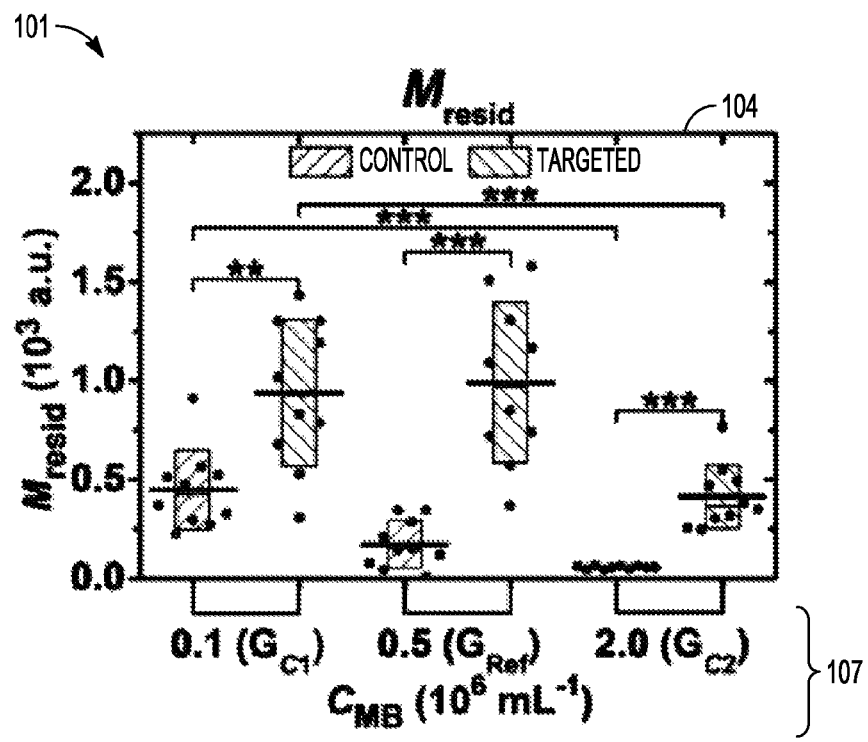
FIG. 7C is a chart illustrating effects of microbubble concentration on the residual signal magnitude parameter ($M_{resid}$ parameter) extracted from control and targeted signal magnitude curves during modulated ARF experiments, in accordance with at least one example of the present subject matter.
Figure 7D:
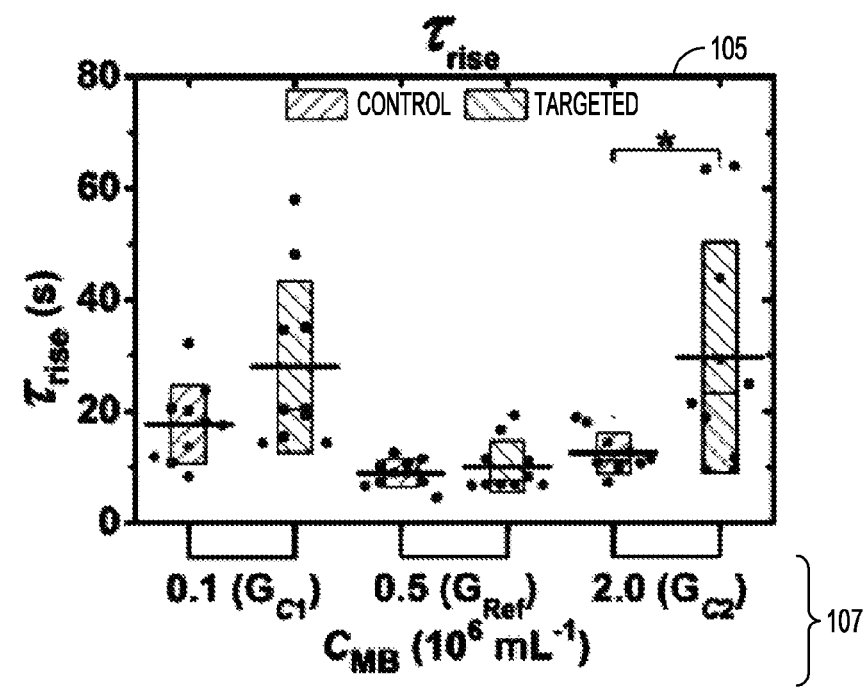
FIG. 7D is a chart illustrating effects of microbubble concentration on the time constant of rise parameter ($\tau_{rise}$ parameter) extracted from control and targeted signal magnitude curves during modulated ARF experiments, in accordance with at least one example of the present subject matter.
Figure 7E:
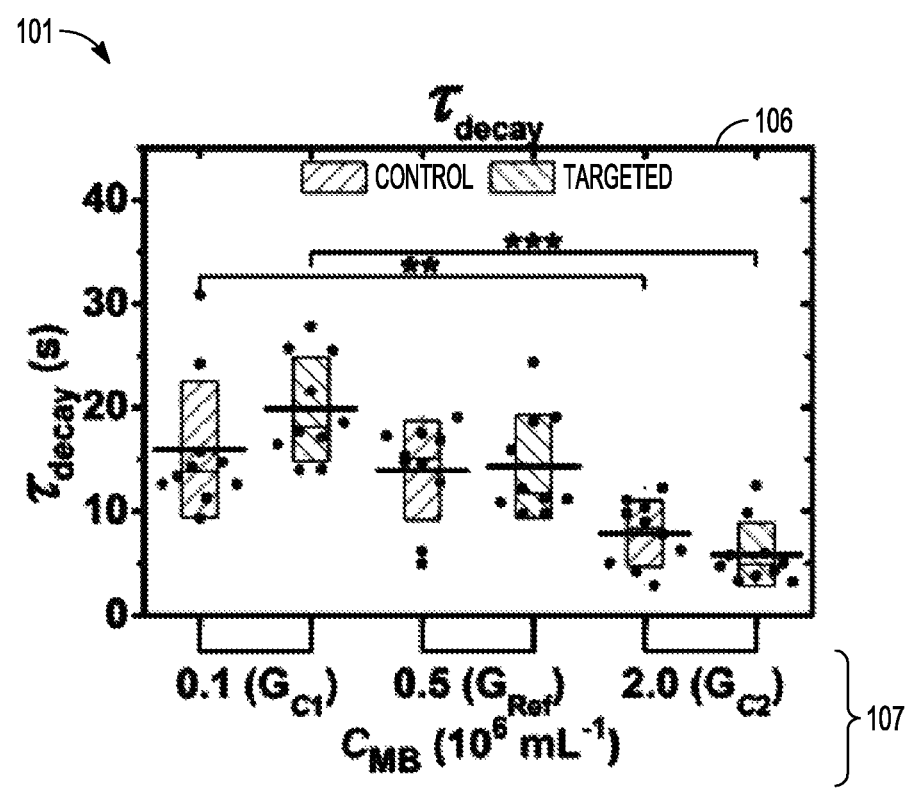
FIG. 7E is a chart illustrating effects of microbubble concentration on the time constant of decay parameter ($\tau_{decay}$ parameter) extracted from control and targeted signal magnitude curves during modulated ARF experiments, in accordance with at least one example of the present subject matter.

FIGS. 7A-E include bar charts illustrating the effects of microbubble concentration 107 on parameters extracted from signal magnitude curves during modulated ARF experiments. The parameters are: $M_{init}$ parameter 26, $M_{satu}$ parameter 34, $M_{resid}$ parameter 36, $\tau_{rise}$ parameter 28, $\tau_{decay}$ parameter 32 ($M_{init}$, $M_{satu}$, $M_{resid}$, $\tau_{rise}$, $\tau_{decay}$) for groups $G_{C1}$, $G_{Ref}$, and $G_{C2}$. FIG. 7A illustrates the effects of microbubble concentration 107 on the $M_{init}$ parameter 26: $M_{init}$ v. concentration 102. FIG. 7B illustrates the effects of microbubble concentration 107 on the $M_{satu}$ parameter 34: $M_{satu}$ v. concentration 103. FIG. 7C illustrates the effects of microbubble concentration 107 on the $M_{resid}$ parameter 36: $M_{resid}$ v. concentration 104. FIG. 7D illustrates the effects of microbubble concentration on the $\tau_{rise}$ parameter 28: $\tau_{rise}$ v. concentration 105. FIG. 7E illustrates the effects of microbubble concentration on the $\tau_{decay}$ parameter 32: $\tau_{decay}$ v. concentration 106. The bar charts show the parameters averaged from 10 trials at different microbubble concentrations 107. In the charts, boxes show the range [mean±standard deviation]. Black lines located at the center of the boxes show the corresponding mean value. Raw data from 10 trials are shown as solid dots overlaying the corresponding boxes. For Student's t-test, *: $p<0.05$, : $p<0.01$, *: $p<0.001$, n=10. Microbubble concentration 107 was the only parameter varied among these three groups ($G_{C1}$, $G_{Ref}$, and $G_{C2}$—see Table 2). In FIG. 7A, the $M_{init}$ parameter 26 of both control and targeted channels monotonically decreased with microbubble concentration 107, with a significant difference observed between the minimum and maximum $M_{init}$ ($p<0.001$, n=10). In FIG. 7B, the $M_{satu}$ parameter 34 in the $G_{C2}$ group was significantly lower than the other two groups ($p<0.001$, n=10). In FIG. 7C, the $M_{resid}$ parameter 36 of targeted channels were significantly higher than that of control channels for all three groups $G_{C1}$, $G_{Ref}$ and $G_{C2}$ <0.01, $p<0.001$, and $p<0.001$, correspondingly; n=10). In addition, the $M_{resid}$ parameter 36 of control channels monotonically decreased with microbubble concentration 107, with a significant difference observed between the minimum and maximum $M_{resid}$ ($p<0.001$, n=10). There was no significant difference for the $\tau_{rise}$ parameter 28 between control and targeted channels in groups $G_{C1}$ and $G_{Ref}$. In FIG. 7D, no significant difference of the $\tau_{decay}$ parameter 32 was found between control and targeted channels for all three groups. In FIG. 7E, however, the $\tau_{decay}$ parameter 32 of both control and targeted channels monotonically decreased with microbubble concentration 107.

Figure 8A:
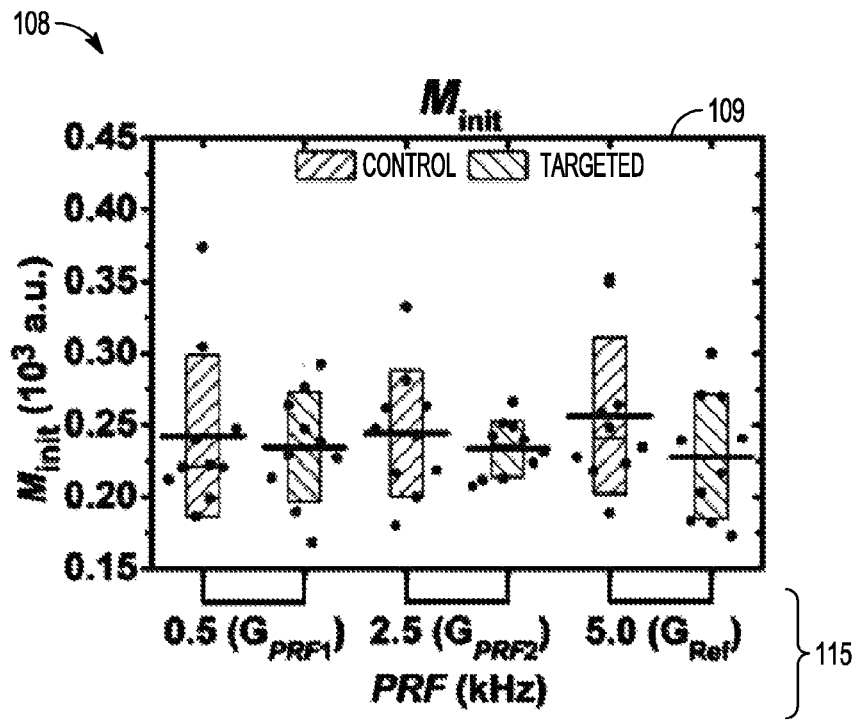
FIG. 8A is a chart illustrating effects of varied ARF intensity (PRF) on the initial signal magnitude parameter ($M_{init}$ parameter) extracted from control and targeted signal magnitude curves during modulated ARF experiments, in accordance with at least one example of the present subject matter.
Figure 8B:
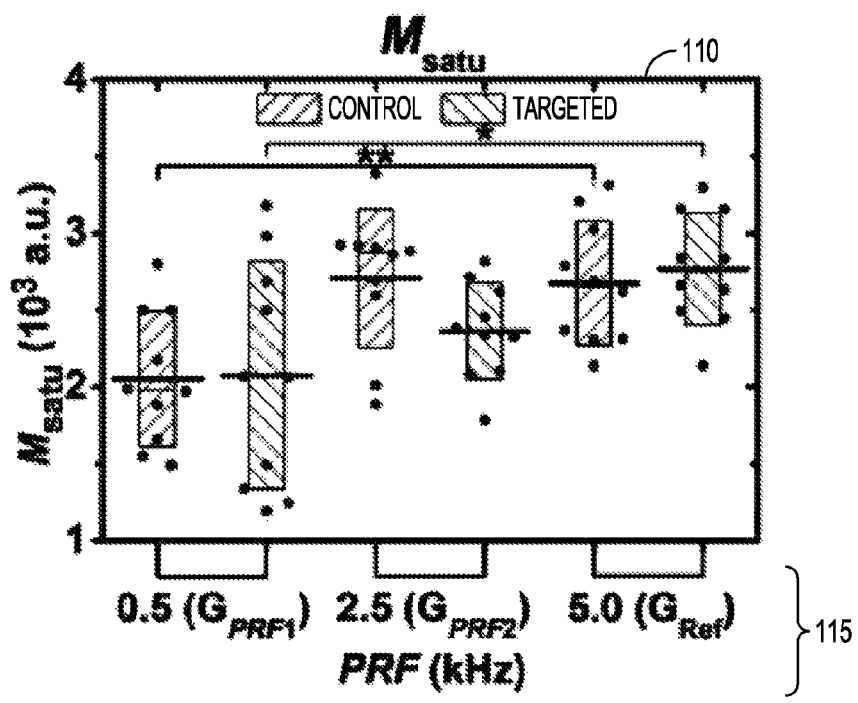
FIG. 8B is a chart illustrating effects of varied ARF intensity (PRF) on the saturated signal magnitude parameter ($M_{satu}$ parameter) parameter extracted from control and targeted signal magnitude curves during modulated ARF experiments, in accordance with at least one example of the present subject matter.
Figure 8C:
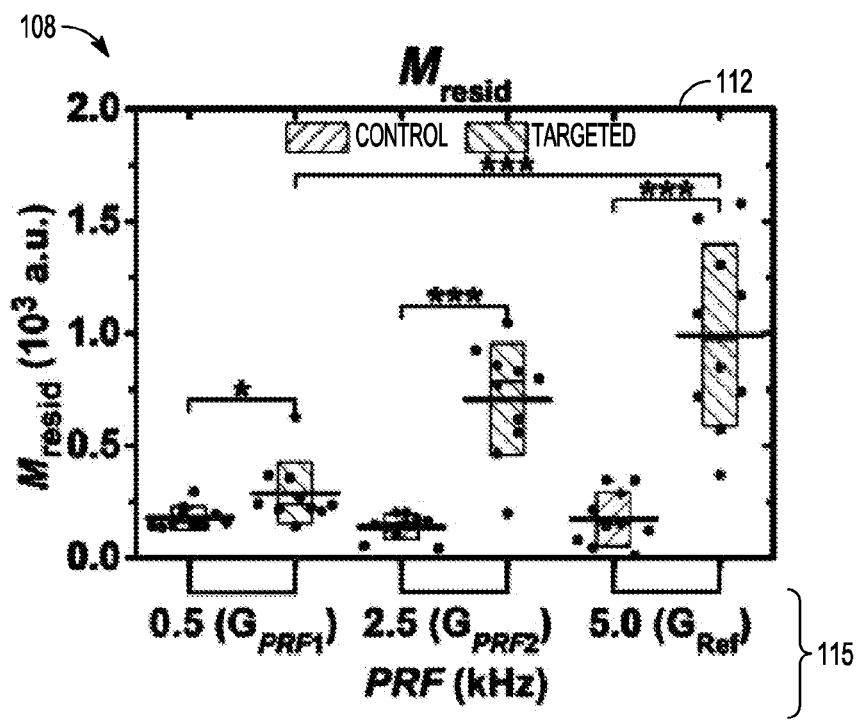
FIG. 8C is a chart illustrating effects of varied ARF intensity (PRF) on the residual signal magnitude parameter ($M_{resid}$ parameter) extracted from control and targeted signal magnitude curves during modulated ARF experiments, in accordance with at least one example of the present subject matter.
Figure 8D:
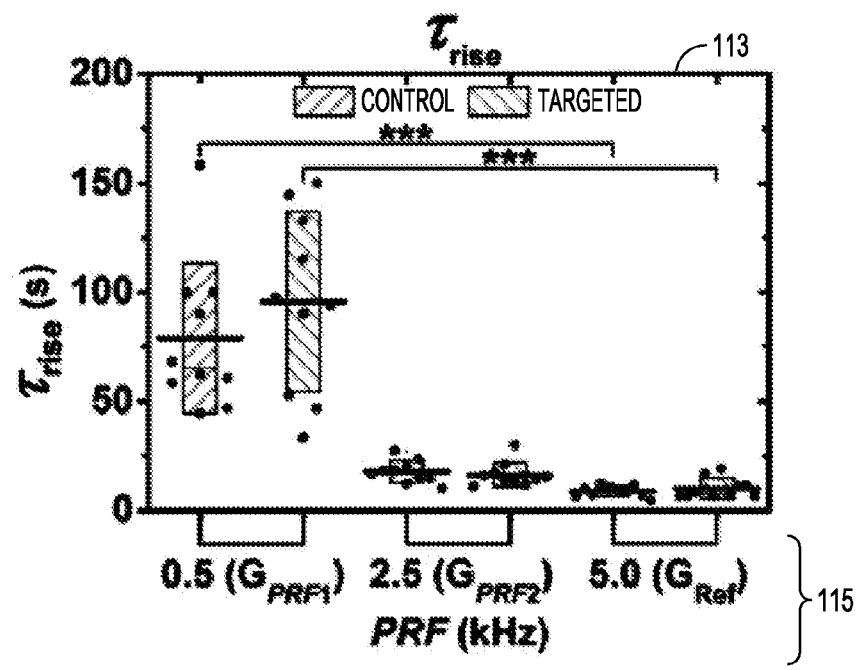
FIG. 8D is a chart illustrating effects of varied ARF intensity (PRF) on the time constant of rise parameter ($\tau_{rise}$ parameter) extracted from control and targeted signal magnitude curves during modulated ARF experiments, in accordance with at least one example of the present subject matter.
Figure 8E:
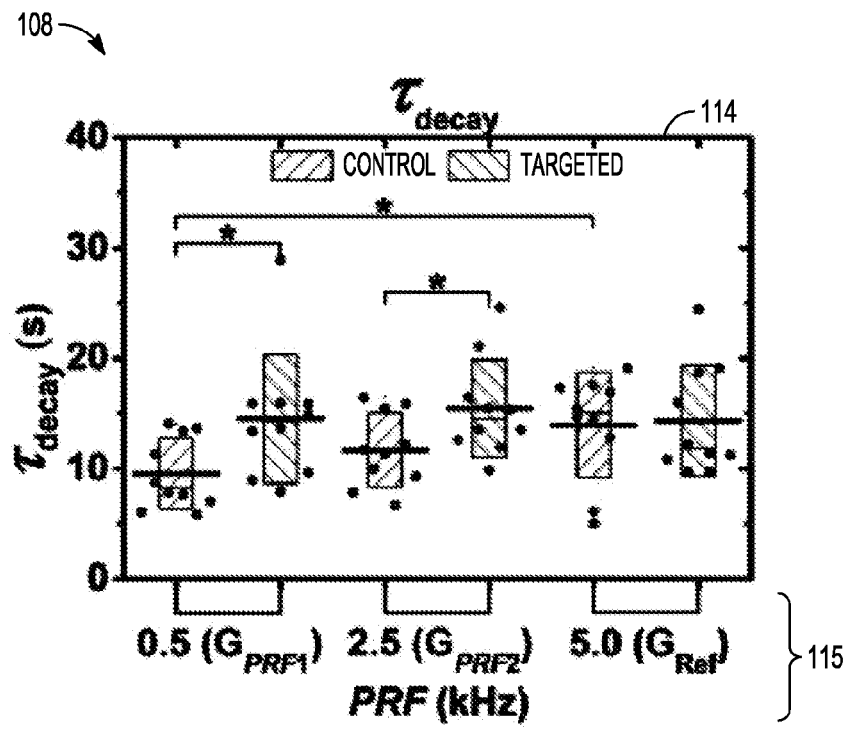
FIG. 8E is a chart illustrating effects of varied ARF intensity (PRF) on the time constant of decay parameter ($\tau_{decay}$ parameter) extracted from control and targeted signal magnitude curves during modulated ARF experiments, in accordance with at least one example of the present subject matter.

FIGS. 8A-E include bar charts illustrating the effects of ARF intensity (pulse repetition frequencies PRF) on parameters extracted from signal magnitude curves during modulated ARF experiments. The parameters are: $M_{init}$ parameter 26, $M_{satu}$ parameter 34, $M_{resid}$ parameter 36, $\tau_{rise}$ parameter 28, $\tau_{decay}$ parameter 32 ($M_{init}$, $M_{satu}$, $M_{resid}$, $\tau_{rise}$, $\tau_{decay}$) for groups $G_{PRF1}$, $G_{PRF2}$ and $G_{Ref}$. FIG. 8A illustrates the effects of ARF intensity on the $M_{init}$ parameter 26: $M_{init}$ v. PRF 109. FIG. 8B illustrates the effects of ARF intensity on the $M_{satu}$ parameter 34: $M_{satu}$ v. PRF 110. FIG. 8C illustrates the effects of ARF intensity on the $M_{resid}$ parameter 36: $M_{resid}$ v. PRF 112. FIG. 8D illustrates the effects of ARF intensity on the $\tau_{rise}$ parameter 28: $\tau_{rise}$ v. PRF 113. FIG. 8E illustrates the effects of ARF intensity on the $\tau_{decay}$ parameter 32: $\tau_{decay}$ v. PRF 114. The bar charts show the parameters averaged from 10 trials at different PRF and fluid channels (e.g. control and targeted channels). In the charts, boxes show the range [mean±standard deviation]. Black lines located at the center of the boxes show the corresponding mean value. Raw data from 10 trials are shown as solid dots overlaying the corresponding boxes. For Student's t-test, *: $p<0.05$, : $p<0.01$, *: $p<0.001$, n=10. The PRF parameter 115 was the only parameter varied among these three groups ($G_{PRF1}$, $G_{PRF2}$ and $G_{Ref}$, see Table 2). In FIG. 8A, no significant difference for the $M_{init}$ parameter was found between control and targeted channels among the different ARF intensity groups. In FIG. 8B, no significant difference for the $M_{satu}$ parameter was found between control and targeted channels among the different ARF intensity groups. The difference between minimum and maximum $M_{satu}$ was significant ($p<0.01$ for control, $p<0.05$ for targeted, n=10). In FIG. 8C, the $M_{resid}$ parameter from targeted channel experiments was significantly higher than for all three groups $G_{PRF1}$, $G_{PRF2}$ and $G_{Ref}$ ($p<0.05$, $p<0.001$, and $p<0.001$, correspondingly; n=10). In addition, the $M_{resid}$ parameter 36 of targeted channel experiments increased monotonically with PRF, with significant difference between the minimum and maximum $M_{resid}$ ($p<0.001$, n=10). In FIG. 8D, the $\tau_{rise}$ parameter 28 for both control and targeted channels decreased monotonically with PRF, with significant difference between the minimum and maximum $\tau_{rise}$ ($p<0.001$, n=10). In FIG. 8E, the $\tau_{decay}$ parameter of targeted channel was significantly higher than that for groups of $G_{PRF1}$ and $G_{PRF2}$ <0.05, n=10). In addition, the $\tau_{decay}$ parameter from control channel experiments increased monotonically with PRF, with significant difference between the minimum and maximum $\tau_{decay}$ ($p<0.05$, n=10).

Figure 9:
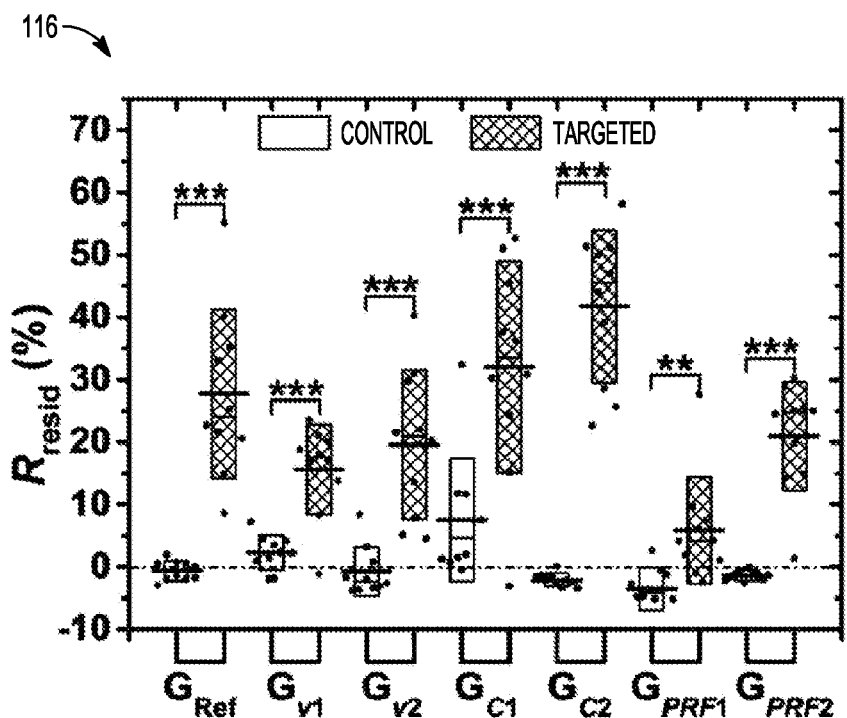
FIG. 9 is a chart illustrating an $R_{resid}$ parameter across the various imaging conditions tested in this disclosure, in accordance with at least one example of the present subject matter.

FIG. 9 illustrates a chart of the $R_{resid}$ parameter percentage plotted to control and targeted channels across the experimental conditions relating to flow, concentration, and ARF intensity 116. In the chart, boxes (empty for control channel and filled for targeted channel) show the range of [mean±standard deviation]. Black lines located at the center of the boxes show the corresponding mean value. Raw data from 10 trials are shown as solid dots overlaid with corresponding boxes. For Student's t-test, : $p<0.01$, *: $p<0.001$, n=10. For control channels at different groups, the $R_{resid}$ parameter was not significantly higher than zero ($p>0.2$) or significantly lower than zero ($p<0.05$) except for groups of $G_{v1}$ and $G_{C1}$ ($p<0.05$; $R_{resid}$=2.3% and 7.6%, respectively). For targeted channels, the $R_{resid}$ parameter was significantly higher than zero and remained above 10% except for the $G_{PRF1}$ group (p=0.057, $R_{resid}$=5.9%). The maximum $R_{resid}$ of targeted channel (41.8%) occurred in the $G_{C2}$ group. For every experimental condition tested in this disclosure, the difference between $R_{resid}$ values of the control and targeted channels were statistically significant ($p<0.01$ for $G_{PRF1}$, $p<0.001$ for all other groups, n=10).

The inventors have disclosed an empirical model for binding dynamics of targeted microbubbles in response to a custom-designed modulated ARF pulse sequence. Experiments were designed and executed systematically to examine the model and study the effects of flow velocity, microbubble concentration, and time-averaged ARF on binding dynamics. Different parameters extracted from the signal magnitude curves of adherent microbubbles were assessed for their ability to differentiate specific from non-specific binding. The ratio of residual to saturation signal ($R_{resid}$), which was only quantifiable using a modulated ARF sequence, was found to best detect targeted adhesion, especially compared with observing the signal magnitude alone in absence of modulated ARF. The primary focus of the modulated acoustic radiation force method proposed in this disclosure is for targeted molecular imaging in large blood vessel environments, such as in the carotid or abdominal aorta.

Generally, the shape of magnitude curve of targeted channels exhibited a good fit to the model as illustrated in FIG. 1. In control experiments, the control peak 76 (see FIGS. 4a and 5) observed experimentally after cessation of ARF was not predicted by the model. One possible explanation for the control peak 76 is related to the effects of aggregating non-specifically bound adherent microbubbles. After cessation of ARF, most adherent microbubbles in targeted channels remained attached at the bottom channel wall due to molecular binding and flow shear forces gradually removed a small portion of targeted adherent microbubbles. However, for control channels, the majority of microbubbles detached from the bottom wall and moved upward due to buoyancy forces immediately after the cessation of ARF. Simultaneously, this layer of microbubbles were washed away and aggregated due to flow shear forces. Consequently, this sudden aggregation of microbubbles along vessel wall resulted in signal magnitude increase control peak 76 (see FIGS. 4A, 5A-F). This control peak 76 can potentially be used to separate non-specific and specific binding of adherent microbubbles.

The effects of flow velocity, microbubble concentration, and ARF on signal magnitude curves are summarized in Table 3. In flow velocity experiments (see FIG. 6), the $\tau_{decay}$ parameter in targeted channels decreased with flow velocity, indicating that molecularly bound adherent microbubbles were washed away more quickly with higher flow shear forces. The $M_{init}$ parameter decreased with microbubble concentration (see FIG. 7) due to a strong shadowing effect that was easily observed in the resulting images. As shown in a previous study, the shadowing is derived from attenuation produced by microbubbles in the channel, which dampens the overall signal magnitude along the bottom channel wall. There was an observed threshold of microbubble concentration between 0.5 and 2.0×10$^6$ mL$^{-1}$, above which the $M_{satu}$ and $M_{resid}$ parameters (targeted) decreased because of excessive shadowing effects from high concentrations of microbubbles. In addition, the $\tau_{decay}$ parameter decreased with microbubble concentration for both targeted and control, suggesting that high microbubble concentration led to a higher reaction rate of the detaching process. The $M_{satu}$ and $M_{resid}$ parameters (targeted) increased with PRF (see FIG. 8) due to increased quantity of microbubbles being pushed to lower channel wall and because the steady-state assumption was better satisfied. The $\tau_{rise}$ parameter decreased with PRF, suggesting that higher intensity of ARF would increase the reaction rate of microbubble attaching process.

lowing assumptions. First, signal magnitude is proportional to microbubble concentration. Second, the $M_{init}$ parameter is the reflection magnitude of the vessel wall without adherent microbubble signal. Third, the $M_{satu}$ parameter is the reflection magnitude when the vessel wall area is completely saturated with adherent microbubbles (including both non-specifically and specifically bound microbubbles). Fourth, most non-specifically bound adherent microbubbles leave the vessel wall with cessation of radiation force while most specifically bound adherent microbubbles remain. Results in this study demonstrated that $R_{resid}$ of targeted experiments were significantly higher than zero and remained above 10% for all groups except in the $G_{PRF1}$ group. This exception was due to an overall lower concentration of microbubbles attached on the wall caused by insufficient ARF (i.e. the third assumption listed above was not valid because steady-state was not reached). In control experiments, the $R_{resid}$ parameter remained below 10% for all groups. Even though the above four assumptions were not directly verified in this study, it was determined that $R_{resid}$ was the best parameter for detecting specific versus non-specific binding and $R_{resid}$, by definition, is independent of absolute signal magnitude. The results also suggest that the value of $R_{resid}$ was an excellent predictor of targeted adhesion without the requirement for a control measurement. This finding was especially true if sufficiently high microbubble concentration and PRF were used. In these instances, any $R_{resid}$ above 10% was representative of targeted adhesion.

The results in FIG. 9 also show that flow shear forces, microbubble concentration and ARF played a big role in $R_{resid}$ values of targeted channels. Even with the same ligand concentration on the vessel wall (controlled in the experimental setup), the $R_{resid}$ parameter in the $G_{v2}$ group was lower than that in the $G_{Ref}$ group due to high flow shear forces, which led to higher detachment of specifically bound microbubbles. Therefore, the $R_{resid}$ parameter is generally an underestimation of the percentage of wall covered by targeted ligands. Because the $R_{resid}$ parameter is independent of absolute signal magnitude and related to the concentration of

TABLE 3

Effects of flow and acoustic conditions

| Parameter | $v_{flow}$ (FIG. 6) | $C_{MB}$ (FIG. 7) | PRF (FIG. 8) |
|---|---|---|---|
| $M_{init}$ | +$^a$ | −$^b$ | =$^c$ |
| $M_{satu}$ | = | Not monotonic | + |
| $M_{resid}$ | = | Control: − | Control: = |
|  |  | Targeted: not monotonic | Targeted: + |
| $\tau_{rise}$ | = | = | − |
| $\tau_{decay}$ | Control: not monotonic | − | Control: + |
|  | Targeted: − |  | Targeted: = |

$^a$Parameter increased with incremental increase in variable
$^b$Parameter decreased with incremental increase in variable
$^c$Parameter was unchanged with incremental increase in variable Results illustrated that $M_{resid}$ is the best parameter among the three parameters ($M_{satu}$, $\tau_{decay}$, and $M_{resid}$) that were considered for detecting specific versus non-specific binding of adherent microbubbles. In addition, results demonstrated the $R_{resid}$ parameter as a potentially more quantitative parameter that would be independent of absolute signal magnitude and thereby more immune to variabilities in tissue attenuation (see FIG. 9). The $R_{resid}$ parameter quantity typically ranges between 0% and 100% and represents a percentage of the total wall surface that retains molecularly targeted microbubbles. This interpretation assumes the folligand coverage along the vessel wall, it can be used for quantitative targeted molecular imaging without the need for control experiments.

In summary, the empirical model provided for binding dynamics of targeted microbubbles in response to modulated ARF pulse sequences was demonstrated to be consistent with experimental results. Higher flow velocity and microbubble concentration led to faster detaching rates of specifically bound adherent microbubbles after cessation of ARF. Higher time-average ARF led to faster attaching rate and higher saturation magnitudes during the application of ARF. The residual microbubble magnitude ($M_{resid}$) of targeted channels was significantly higher than that of control channels at all flow and acoustic conditions in this study. The ratio of residual to saturation signal ($R_{resid}$) was observed to be an excellent parameter for detection of targeted adhesion without the need for separate control measurements. If certain assumptions are met, then $R_{resid}$ provides a quantity related to the percentage of remaining specifically bound adherent microbubbles along the vessel wall. Therefore, these results suggest that modulated ARF sequences and extraction of the $R_{resid}$ parameter has potential for use in targeted molecular imaging and as a means to achieve quantitative measures of ligand concentration in real-time, using relatively short imaging protocols (approximately 3 min) that do not require separate control populations or waiting periods.

Three parameters extracted directly from the single magnitude curves ($M_{satu}$, $\tau_{decay}$ and $M_{resid}$) can potentially be used to differentiate specific from non-specific binding of adherent microbubbles. Typical approaches to real-time targeted molecular imaging seek to quantify the presence of specifically bound adherent microbubbles without modulating ARF. In these approaches, the image intensity of targeted microbubbles at a given time is measured and compared against control. The $M_{satu}$ parameter is an example of a parameter used in standard approaches. In contrast, the dynamic response of adherent microbubbles under modulated ARF is closely related to the binding strength of ligand-receptor pairs. Specifically bound adherent microbubbles have much higher binding strength than non-specifically bound ones, and therefore require higher external forces (buoyancy force, flow shear force, etc.) to detach. As a result, after the cessation of ARF, the remaining number of specifically bound microbubbles (proportional to $M_{resid}$) is proposed to be higher than that of non-specifically bound microbubbles.

The results of the three parameters ($M_{satu}$, $\tau_{decay}$, and $M_{resid}$) for both targeted and control are summarized in Table 4. Among the three parameters, only the $M_{resid}$ parameter exhibited consistent significant differences between targeted and control under all flow and acoustic conditions listed in Table 2. It was therefore the best parameter for detecting specific versus non-specific binding of adherent microbubbles. In these experiments, we observed that the $M_{satu}$ parameter was not a reliable indicator of targeted binding. Instead, modulation of ARF with measures of $M_{resid}$ was required to distinguish targeted versus control.

TABLE 4

Parameter ability to differentiate targeted from control Group

| Parameter | $G_{v1}$, $G_{Ref}$, $G_{v2}$ (FIG. 6) | $G_{C1}$, $G_{Ref}$, $G_{C2}$ (FIG. 7) | $G_{PRF1}$, $G_{PRF2}$, $G_{Ref}$ (FIG. 8) |
|---|---|---|---|
| $M_{satu}$ | −[a] | − | − |
| $\tau_{decay}$ | − | − | − |
| $M_{resid}$ | +[b] | + | + |

[a] No significant difference between targeted and control among all three corresponding groups
[b] Significant difference between targeted and control among all three corresponding groups The present inventors have contemplated a variety of ultrasound related systems and methods that can be utilized as part of implementing or practicing aspects of the various examples described above of the present disclosure.

Figure 10:
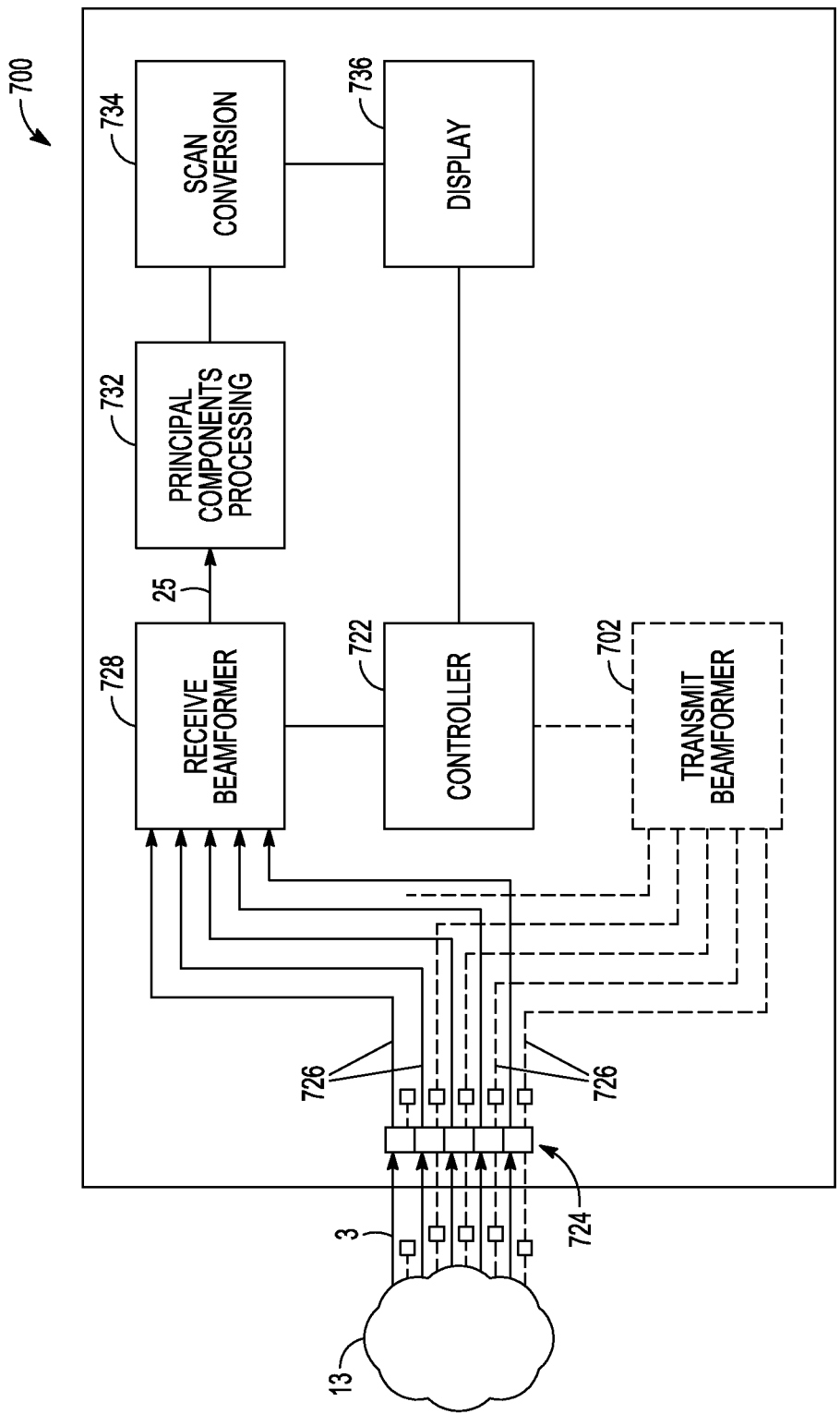
FIG. 10 illustrates a schematic representation of an ultrasound system, in accordance with at least one example of the present subject matter.

FIG. 10 is a basic, schematic representation of an ultrasound system 700 according to an aspect of an example of the present invention that is referred to in order to generally describe the operations of an ultrasound system to produce an image of an object 13. System 700 may optionally include a transmit beamformer 702 which may include input thereto by controller 722 to send electrical instructions to the transducer 724 as to the specifics of the ultrasonic waves to be emitted by the transducer 724. Alternatively, system 700 can be a receive only system and the emitted waves may be directed to the object 13 from an external source.

In either case, echoes 3 reflected by the object 13 (and surrounding environment) are received by the transducer 724 and converted to electrical (e.g., radio frequency (RF)) signals 726 that are input to receive beamformer 728. A controller 722 may be external of the beamformer 728, as shown, or integrated therewith. The controller 722 can automatically and dynamically change the distances at which scan lines are performed (when a transmit beamformer 702 is included) and can automatically and dynamically control the receive beamformer 728 to receive signal data for scan lines at predetermined distances. Distance/depth can be calculated assuming a constant speed of sound in tissue (e.g., 1540 m/s or as desired or required) and then time of flight can be recorded such that the returning echoes have a known origination. The summed RF lines output by the receive beamformer 728 can be input to a principal components processing module 732, which may be separate from and controlled by, or incorporated in controller 722. Principal components module 732 can process received echo data.

The assembled output may be input into a scan converter module 734. The image formed within the scan converter 734 can be displayed on a display 736. Although FIG. 10 has been described as an ultrasound system, it is noted that a transducer 724 (which can be configured as an array) may alternatively be a transducer for converting electrical energy to forms of energy other than ultrasound and vice versa, including, but not limited to radio waves (e.g., where system 700 is configured for RADAR), visible light, infrared, ultraviolet, and/or other forms of sonic energy waves, including, but not limited to SONAR, or some other arbitrary signal of arbitrary dimensions greater than one (such as, for example, a signal that is emitted by a target).

Figure 11:
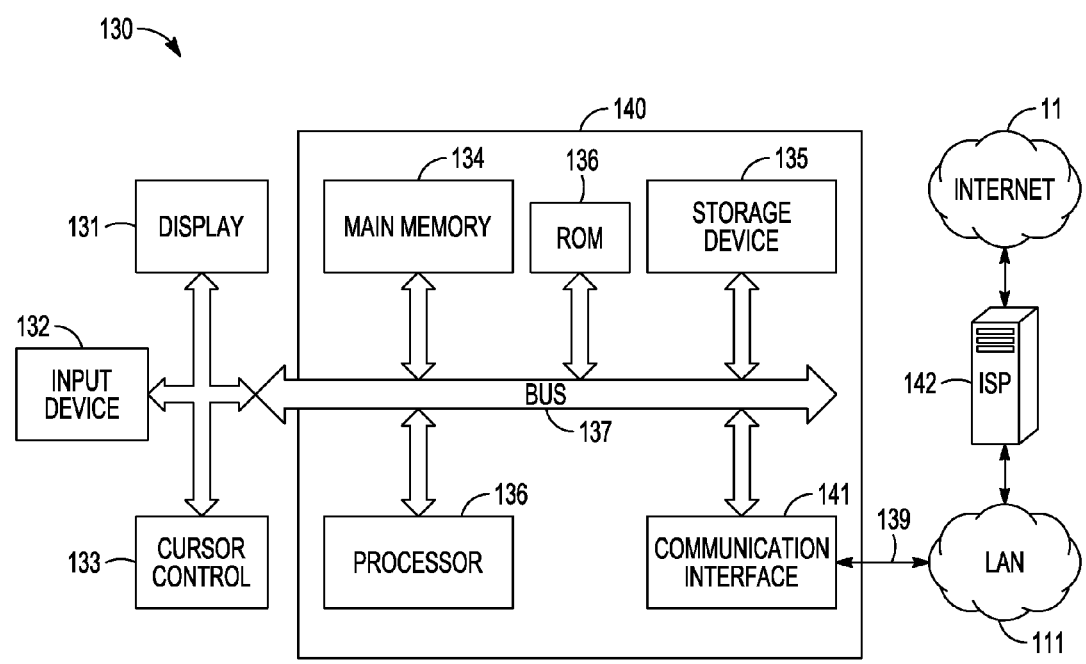
FIG. 11 illustrates a block diagram of a system including a computer system and an associated Internet connection, in accordance with at least one example of the present subject matter.

FIG. 11 is a block diagram that illustrates a system 130 including a computer system 140 and the associated Internet 11 connection upon which an example may be implemented. FIG. 11 illustrates a typical computer system, all or a portion of which may be incorporated into a system according to an example of the present invention. As will be discussed in greater detail below, the computer system may include any number of processors (also referred to as central processing units, or CPUs) that are coupled to storage devices including primary storage (typically a random access memory, or RAM), primary storage (typically a read only memory, or ROM). Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 11. The system 140 may be used as a portable electronic device such as a notebook/laptop computer, a media player (e.g., MP3 based or video player), a cellular phone, a Personal Digital Assistant (PDA), a portion of an ultrasound device, an image processing device (e.g., a digital camera or video recorder), and/or any other handheld computing devices, or a combination of any of these devices.

Note that while FIG. 11 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 11 may, for example, be an Apple Macintosh computer or Power Book, or an IBM compatible PC. A computer system 140 can include a bus 137, an interconnect, or other communication mechanism for communicating information, and a processor 138, commonly in the form of an integrated circuit, coupled with the bus 137 for processing information and for executing the computer executable instructions. The computer system 140 can also include a main memory 134, such as a Random Access Memory (RAM) or other dynamic storage device, coupled to the bus 137 for storing information and instructions to be executed by the processor 138.

A main memory 134 also may be used for storing temporary variables or other intermediate information during execution of instructions to be executed by processor 138. The computer system 140 can further include a Read Only Memory (ROM) 136 (or other non-volatile memory) or other static storage device coupled to the bus 137 for storing static information and instructions for the processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, can be coupled to the bus 137 for storing information and instructions. The hard disk drive, magnetic disk drive, and optical disk drive can be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

The computer system 140 may be coupled via the bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, can be coupled to the bus 137 for communicating information and command selections to the processor 138. Another type of user input device can be a cursor control 133, such as a mouse, a trackball, or cursor direction keys for communicating direction information and command selections to the processor 138 and for controlling cursor movement on the display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one example, those methods and techniques are performed by computer system 140 in response to the processor 138 executing one or more sequences of one or more instructions contained in the main memory 134. Such instructions may be read into main memory 134 from another computer-readable medium, such as the storage device 135. Execution of the sequences of instructions contained in the main memory 134 can cause the processor 138 to perform the process steps described herein. In alternative examples, hard-wired circuitry may be used in place of or in combination with software instructions to implement the arrangement. Thus, examples of the invention are not limited to any specific combination of hardware circuitry and software.

The term "computer-readable medium" (or "machine-readable medium") as used herein is an extensible term that refers to any medium or any memory, that participates in providing instructions to a processor, (such as the processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that can comprise the bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on the bus 137. The bus 137 can carry the data to main memory 134, from which the processor 138 can retrieve and execute the instructions. The instructions received by main memory 134 may optionally be stored on storage device 135 either before or after execution by the processor 138.

Computer system 140 also includes a communication interface 141 coupled to the bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by the processor 138 as it is received, and/or stored in storage device 135, or other non-volatile storage for later execution. In this manner, computer system 140 may obtain application code in the form of a carrier wave.

Figure 12:
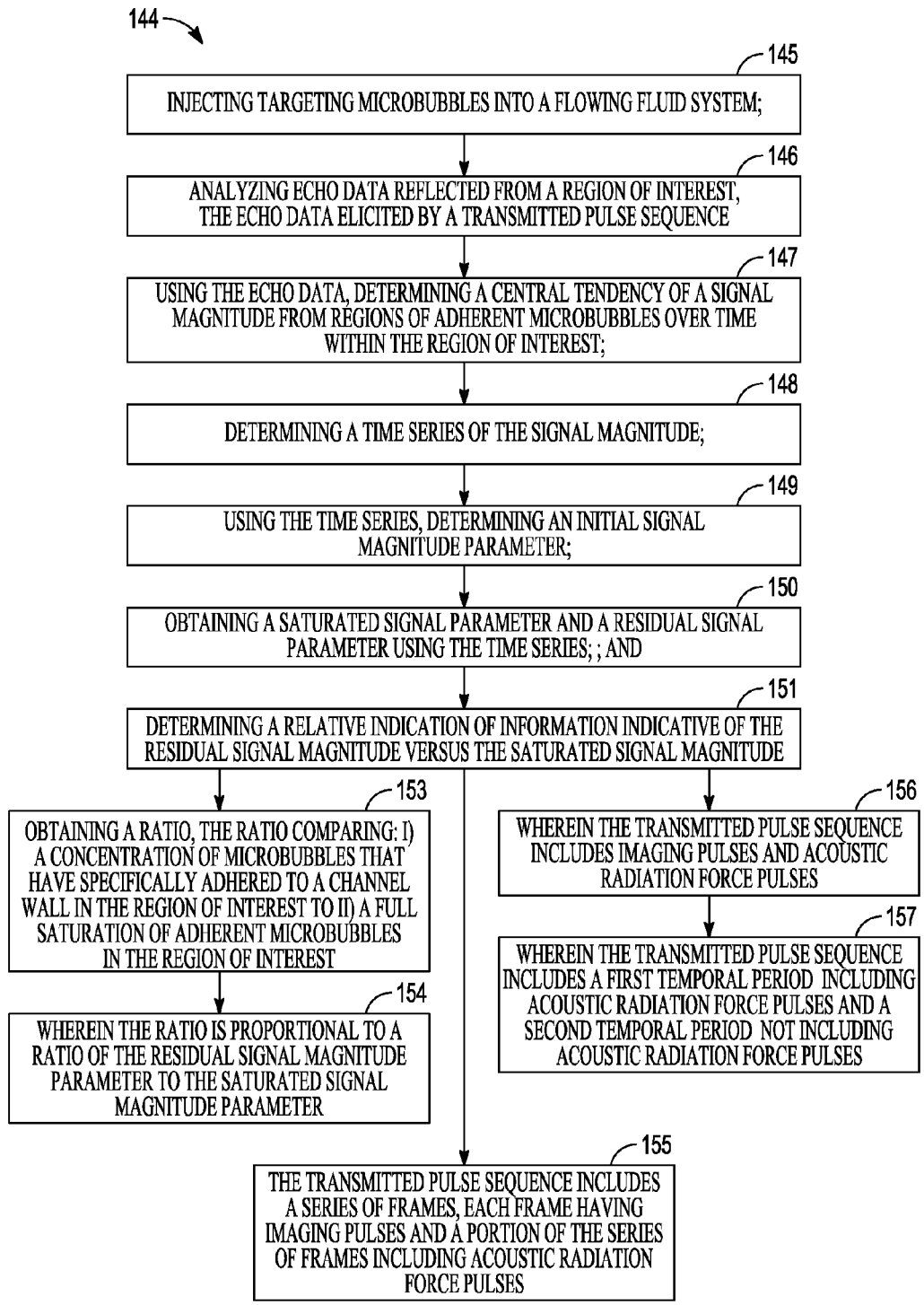
FIG. 12 illustrates a flowchart of an example of one or more methods of measuring microbubble dynamics, in accordance with at least one example of the present subject matter.

FIG. 12 illustrates a flowchart of an example of one or more methods of measuring microbubble dynamics 144, that can include: injecting targeting microbubbles into a flowing fluid system 145; analyzing echo data reflected from a region of interest, the echo data elicited by a transmitted pulse sequence 146; using the echo data, determining a central tendency of a signal magnitude from regions of adherent microbubbles over time within the region of interest 147; determining a time series of the signal magnitude 148; using the time series, determining an initial signal magnitude parameter 149; obtaining a saturated signal parameter and a residual signal parameter using the time series 150; and determining a relative indication of information indicative of the residual signal magnitude versus the saturated signal magnitude 151.

In addition, FIG. 12 illustrates additional method steps that can optionally branch from elements 145-151. In an example, a method measuring microbubble dynamics can include: the method of elements 145-151 further including: obtaining a ratio, the ratio comparing: i) a concentration of microbubbles that have specifically adhered to a channel wall in the region of interest to ii) a full saturation of adherent microbubbles in the region of interest 153. In an example, a method measuring microbubble dynamics can include: the method of elements 145-151, 153 and further including; wherein the ratio is proportional to a ratio of the residual signal magnitude parameter to the saturated signal magnitude parameter 154. In an example, a method measuring microbubble dynamics can include: the method of elements 145-151 further including: wherein the transmitted pulse sequence includes a series of frames, each frame having imaging pulses and a portion of the series of frames including acoustic radiation force pulses 155. In an example, a method measuring microbubble dynamics can include: the method of elements 145-151 further including: wherein the transmitted pulse sequence includes imaging pulses and acoustic radiation force pulses 156. In an example, a method measuring microbubble dynamics can include: the method of elements 145-151, 156 and further including; wherein the transmitted pulse sequence includes a first temporal period including acoustic radiation force pulses and a second temporal period not including acoustic radiation force pulses 157.

The concept of binding dynamics of targeted microbubbles in response to modulated ARF pulse sequences has been achieved herein according to an aspect of an example of the present invention. According to an aspect of an example of the present invention, higher flow velocity and microbubble concentration led to faster detaching rates of specifically bound adherent microbubbles after cessation of ARF. According to an aspect of an example of the present invention, higher time-average ARF led to faster attaching rate and higher saturation magnitudes during the application of ARF. As seen from the algorithms, experiments, systems, and methodology requirements discussed herein, the present invention or portions thereof may be implemented and utilized at least in part with the related processors, networks, computer systems, internet, and components and functions according to the examples disclosed herein.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An ultrasound system, comprising:
a receive beamformer configured to receive echo data from a transducer, wherein the echo data is reflected from a region of interest, wherein the echo data is elicited by a transmitted pulse sequence, wherein the transmitted pulse sequence includes imaging pulses and acoustic radiation force pulses, wherein the transmitted pulse sequence includes a first temporal period including acoustic radiation force pulses and a second temporal period not including acoustic radiation force pulses;
a processor coupled to the receive beamformer, the processor configured to:
determine a central tendency of a signal magnitude from regions of adherent microbubbles over time within the region of interest, using the echo data;
determine a time series of the central tendency of the signal magnitude;
determine an initial signal magnitude parameter, using the time series;
obtain a saturated signal magnitude parameter and a residual signal magnitude parameter using the time series, wherein the residual signal magnitude parameter is obtained from the second temporal period;
determine a relative indication of information indicative of the residual signal magnitude parameter versus the saturated signal magnitude parameter based on the initial signal magnitude parameter, the saturated signal magnitude parameter, and the residual signal magnitude parameter; and
a display configured to display the relative indication, wherein the relative indication is indicative of a concentration of specifically adherent microbubbles in the region of interest.

2. The ultrasound system of claim 1, wherein the relative indication includes a ratio, wherein the ratio is proportional to a ratio of the residual signal magnitude parameter minus the initial signal magnitude parameter to the saturated signal magnitude parameter minus the initial signal magnitude parameter.

3. The ultrasound system of claim 2, wherein the ratio compares: i) a concentration of microbubbles that have specifically adhered to a channel wall in the region of interest to ii) a full saturation of adherent microbubbles in the region of interest.

4. The ultrasound system of claim 2, wherein the ratio is $R_{resid}$ and expressed as a percentage is:

$$R_{resid} = \left( \frac{M_{resid} - M_{init}}{M_{satu} - M_{init}} \right) \times 100\%,$$

wherein $M_{init}$ is the initial signal magnitude parameter, $M_{satu}$ is the saturated signal magnitude parameter, and $M_{resid}$ is the residual signal magnitude parameter.

5. The ultrasound system of claim 1, wherein the transmitted pulse sequence includes a series of frames, each frame including an imaging pulse and a portion of the frames including an acoustic radiation force pulse.

6. The ultrasound system of claim 1, wherein the transmitted pulse sequence is at least 100 seconds in duration, the first temporal period of the transmitted pulse sequence having an initial temporal period not including acoustic radiation force pulses.

7. The ultrasound system of claim 1, wherein the transmitted pulse sequence is at least 180 seconds in duration, the first temporal period of the transmitted pulse sequence having an initial temporal period of 10 seconds duration not including acoustic radiation force pulses.

8. The ultrasound system of claim 1, wherein the first temporal period includes a signal magnitude dynamic response known as $M_{rise}(t)$, wherein M(t) is a quantity that is directly proportional to adherent microbubble concentration such that $M_{rise}(t)$ can be described as:

$$M_{rise}(t) = M_{satu} - (M_{satu} - M_{init}) \times e^{-\frac{t}{\tau_{rise}}},$$

wherein $M_{init}$ is the initial signal magnitude parameter, $M_{satu}$ is the saturated signal magnitude parameter and $M_{resid}$ is the residual signal magnitude parameter, wherein $\tau_{rise}$ is a time constant of rise parameter and (t) is time, and the second temporal period includes a signal magnitude decay response known as $M_{decay}(t)$, that can be described as:

$$M_{decay}(t) = M_{resid} - (M_{resid} - M_{max}) \times e^{-\frac{t}{\tau_{decay}}},$$

wherein $M_{max}$ is a maximum signal magnitude measured immediately after a cessation of the acoustic radiation force and $\tau_{decay}$ is a time constant of decay parameter.

9. A method of measuring microbubble dynamics comprising:
injecting targeting microbubbles into a flowing fluid system;
analyzing echo data reflected from a region of interest in the flowing fluid system, the echo data elicited by a transmitted pulse sequence, wherein the transmitted pulse sequence includes imaging pulses and acoustic radiation force pulses, wherein the transmitted pulse sequence includes a first temporal period including acoustic radiation force pulses and a second temporal period not including acoustic radiation force pulses;
using the echo data, determining a central tendency of a signal magnitude from regions of adherent microbubbles over time within the region of interest;
determining a time series of the central tendency of the signal magnitude;
determining an initial signal magnitude parameter, using the time series;
obtaining a saturated signal magnitude parameter and a residual signal magnitude parameter using the time series, wherein the residual signal magnitude parameter is obtained from the second temporal period;
determining a relative indication of information indicative of the residual signal magnitude parameter versus the saturated signal magnitude parameter based on the initial signal magnitude parameter, the saturated signal magnitude parameter, and the residual signal magnitude parameter; and
displaying the relative indication, wherein the relative indication is indicative of a concentration of specifically adherent microbubbles in the region of interest.

10. The method claim 9, wherein the relative indication includes a ratio, wherein the ratio is proportional to a ratio of the residual signal magnitude parameter minus the initial signal magnitude parameter to the saturated signal magnitude parameter minus the initial signal magnitude parameter.

11. The method of claim 10, wherein the ratio compares: i) a concentration of microbubbles that have specifically adhered to a channel wall in the region of interest to ii) a full saturation of adherent microbubbles in the region of interest.

12. The method of claim 9, wherein the transmitted pulse sequence includes a series of frames, each frame having imaging pulses and a portion of the series of frames including acoustic radiation force pulses.

13. The method of claim 9, wherein the transmitted pulse sequence is at least 100 seconds in duration, the first temporal period of the transmitted pulse sequence having an initial temporal period not including acoustic radiation force pulses.

14. The method of claim 9, wherein the transmitted pulse sequence is at least 180 seconds in duration, the first temporal period of the transmitted pulse sequence having an initial temporal period of 10 seconds duration not including acoustic radiation force pulses.

15. A non-transitory machine readable medium embodying a set of instructions that, when executed by a processor, cause the processor to perform operations comprising:
analyzing echo data reflected from a region of interest of a fluid flowing system, the echo data elicited by a transmitted pulse sequence, wherein the transmitted pulse sequence includes imaging pulses and acoustic radiation force pulses, wherein the transmitted pulse sequence includes a first temporal period including acoustic radiation force pulses and a second temporal period not including acoustic radiation force pulses, wherein the transmitted pulse sequence is directed at the region of interest after injecting the flowing fluid system with targeting microbubbles;
using the echo data, determining a central tendency of a signal magnitude from regions of adherent microbubbles over time within the region of interest;
determining a time series of the central tendency of the signal magnitude;
determining an initial signal magnitude parameter, using the time series;
obtaining a saturated signal magnitude parameter and a residual signal magnitude parameter using the time series, wherein the residual signal magnitude parameter is obtained from the second temporal period;
determining a relative indication of information indicative of the residual signal magnitude parameter versus the saturated signal magnitude parameter based on the initial signal magnitude parameter, the saturated signal magnitude parameter, and the residual signal magnitude parameter; and
displaying the relative indication, wherein the relative indication is indicative of a concentration of specifically adherent microbubbles in the region of interest.

16. The non-transitory machine readable medium of claim 15 wherein the relative indication includes a ratio, wherein the ratio is proportional to a ratio of the residual signal magnitude parameter minus the initial signal magnitude parameter to the saturated signal magnitude parameter minus the initial signal magnitude parameter.

17. The non-transitory machine readable medium of claim 16, wherein the ratio compares: i) a concentration of microbubbles that have specifically adhered to a channel wall in the region of interest to ii) a full saturation of adherent microbubbles in the region of interest.

18. The non-transitory machine readable medium of claim 15, wherein the transmitted pulse sequence is at least 100 seconds in duration, the first temporal period of the transmitted pulse sequence having an initial temporal period not including acoustic radiation force pulses.

19. The non-transitory machine readable medium of claim 15, wherein the transmitted pulse sequence is at least 180 seconds in duration, the first temporal period of the transmitted pulse sequence having an initial temporal period of 10 seconds duration not including acoustic radiation force pulses.

* * * * *